(12) United States Patent
Bouillot et al.

(10) Patent No.: US 10,611,756 B2
(45) Date of Patent: *Apr. 7, 2020

(54) METHOD OF TREATING PANCREATITIS USING 1,4-BENZOXAZINE DERIVATIVES

(71) Applicant: GLAXOSMITHKLINE INTELLECTUAL PROPERTY DEVELOPMENT LIMITED, Brentford, Middlesex (GB)

(72) Inventors: Anne Marie Jeanne Bouillot, Villebon-sur-Yvette (FR); Alexis Denis, Villebon-sur-Yvette (FR); John Liddle, Stevenage (GB); Olivier Mirguet, Villebon-sur-Yvette (FR); Ann Louise Walker, Stevenage (GB)

(73) Assignee: The University Court of The University of Edinburgh, Edinburgh (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/271,332

(22) Filed: Feb. 8, 2019

(65) Prior Publication Data

US 2019/0169178 A1  Jun. 6, 2019

Related U.S. Application Data

(63) Continuation of application No. 15/574,947, filed as application No. PCT/EP2016/061173 on May 19, 2016, now Pat. No. 10,246,447.

(30) Foreign Application Priority Data

May 22, 2015 (GB) .................................. 1508864.4

(51) Int. Cl.
| | | |
|---|---|---|
| *A61K 31/00* | (2006.01) |
| *A61K 31/538* | (2006.01) |
| *A61P 1/16* | (2006.01) |
| *A61P 1/18* | (2006.01) |
| *A61P 11/00* | (2006.01) |
| *A61P 13/12* | (2006.01) |
| *A61P 25/00* | (2006.01) |
| *A61P 29/00* | (2006.01) |
| *A61P 31/00* | (2006.01) |
| *C07D 413/12* | (2006.01) |

(52) U.S. Cl.
CPC ................................. *C07D 413/12* (2013.01)

(58) Field of Classification Search
CPC ......... A61K 31/00; A61K 31/538; A61P 1/16; A61P 1/18; A61P 11/00; A61P 13/12; A61P 25/00; A61P 29/00; A61P 31/00
See application file for complete search history.

(56) References Cited

FOREIGN PATENT DOCUMENTS

| WO | WO 97/17317 A1 | 5/1997 |
| WO | WO 2013/151707 A1 | 10/2013 |
| WO | WO 2015/091647 A1 | 6/2015 |

*Primary Examiner* — Bruck Kifle
(74) *Attorney, Agent, or Firm* — Casimir Jones, S.C.; Lisa V. Mueller

(57) ABSTRACT

The present invention relates to methods and/or uses for treating pancreatitis, kidney diseases and other various disorders as described herein, for conditions or disorders mediated by KMO inhibitors, which comprises administering 6-chlorobenzoxazine compounds of Formula (I):

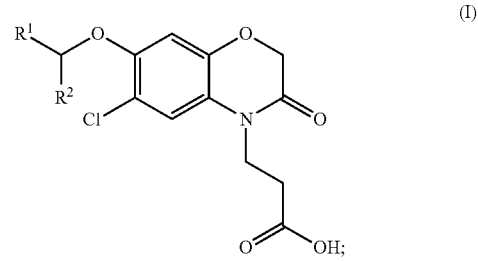

or pharmaceutically acceptable salts and/or corresponding pharmaceutical compositions thereof.

11 Claims, No Drawings

METHOD OF TREATING PANCREATITIS USING 1,4-BENZOXAZINE DERIVATIVES

FIELD OF THE INVENTION

The present invention relates to methods and/or uses for treating pancreatitis, kidney diseases and other various disorders as described herein, for conditions or disorders mediated by KMO inhibitors, which comprises administering 6-chlorobenzoxazine compounds of Formula (I) or pharmaceutically acceptable salts or pharmaceutical compositions thereof.

BACKGROUND OF THE INVENTION

Kynurenine monooxygenase (KMO) is a flavin adenine dinucleotide (FAD) dependent monooxygenase located on the outer mitochondrial membrane. KMO is known to oxidise L-Kynurenine (KYN) to 3-hydroxykynurenine (3HK) as part of the major route of catabolism of tryptophan. 3HK is then converted to 3-hydroxyanthranilic acid and quinolinic acid by kynureninase (KYNU) and 3-hydroxyanthranilate 3,4-dioxygenase (3-HAAO).

KMO is highly expressed in tissues including the liver, placenta, kidney [Alberati-Giani, FEBS Lett. 410:407-412 (1997)] endothelial cells and monocytes and at a lower level in microglia and macrophages in the brain.

Increased levels of 3HK and quinolinic acid and reduced levels of Kynurenic acid (KYNA), which is formed from kynurenine by an alternative pathway, have been implicated in a number of diseases including Huntington's Disease, Parkinson's Disease, Alzheimer's Disease, amyotrophic lateral sclerosis (ALS) [Amaral, Outeiro et Al. Journal of Molecular medicine 2013: 91(6): 705-713] and Acute Pancreatitis [Mole, McFerran et al. British Journal of Surgery 2008: 95: 855-867]. In the CNS 3-HK and quinolinic acid have been shown to be neurotoxic and KYNA to have neuroprotective effects. Inhibition of KMO oxidative activity would therefore be expected to result in reduced levels of 3-HK and quinolinic acid and increased levels of KYNA and to potentially show benefit for these diseases.

There is a large body of evidence showing that tryptophan metabolism is also altered in a range of acute injury settings. For instance, increased kynurenine levels have been associated with the development of sepsis following trauma [Pellegrin, 2005, Logters, 2009], while increased levels of both kynurenine and 3-HK correlate with the development of organ failure in acute pancreatitis [Mole, McFerran et al. British Journal of Surgery 2008: 95: 855-867]. This dysregulation of tryptophan metabolism is in part accounted for by the induction of indolamine 2,3 dioxygenase (IDO, the enzyme that converts tryptophan to N-formyl kynurenine)) as part of the inflammatory cascade, but the development of organ dysfunction appears dependent on the downstream metabolites [Mole, McFerran et al. British Journal of Surgery 2008: 95: 855-867].

Acute pancreatitis (AP) results from local injury to the organ driven by factors such as excessive alcohol consumption or gallstones. The arising abdominal pain is extremely severe, and patients will invariably present to an emergency department rapidly following onset of an attack, with elevation of serum amylase used as a diagnostic. In the majority of cases, the disease is self limiting, and the pain resolves within 24-36 hours. However for the remaining 20-30% of patients a systemic inflammatory response occurs, resulting in rapid progression to multiple organ dysfunction (MOD). This leads to a prolonged stay in ICU (averaging 17 days), with a mortality rate of over 30%. Despite this high unmet need and the seriousness of the disease, there are no effective treatments available, with current standard of care being purely supportive.

WO2013016488, WO2011091153, WO2010017132, WO2010017179, WO2010011302, WO2008022286 and WO2008022281 describe inhibitors of KMO for targeting neurodegenerative disorders or diseases; EP1475385, EP1424333 describe inhibitors of KMO for targeting degenerative and inflammatory conditions. There remains a need for KMO inhibitors for use in the treatment of various conditions or disorders mediated by KMO such as acute pancreatitis and other conditions associated with systemic inflammatory response syndrome (SIRS).

A class of compounds has now been found which are inhibitors of KMO. Inhibitors of KMO may be useful in the treatment of various conditions or disorders such as, for example, acute pancreatitis and acute conditions associated with systemic inflammatory response syndrome (SIRS).

SUMMARY OF THE INVENTION

In general, the present invention relates to methods and/or uses for treating pancreatitis, kidney diseases and other various disorders as described herein, for conditions or disorders mediated by KMO inhibitors, which comprises administering 6-chlorobenzoxazine compounds of Formula (I) or pharmaceutically acceptable salts or pharmaceutical compositions thereof.

The invention is directed to methods and/or uses for treating pancreatitis, kidney diseases and other various disorders as described herein, for conditions or disorders mediated by KMO inhibitors, which comprises administering 6-chlorobenzoxazine compounds of Formula (I):

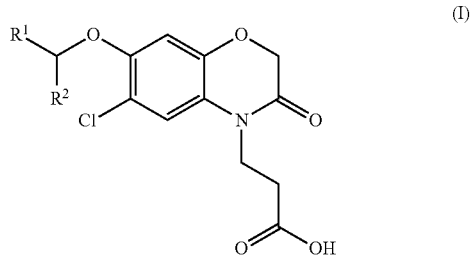

where $R^1$ and $R^2$ are as defined below herein; or a pharmaceutically acceptable salt or corresponding pharmaceutical compositions thereof.

Certain compounds have been shown to be KMO inhibitors. Compounds which inhibit KMO may be useful in the treatment of various disorders, for example acute pancreatitis, chronic kidney disease, acute kidney disease, acute kidney injury, other conditions associated with systemic inflammatory response syndrome (SIRS), Huntington's disease, Alzheimer's disease, spinocerebellar ataxias, Parkinson's disease, AIDS-dementia complex, HIV infection, amylotrophic lateral sclerosis (ALS), depression, schizophrenia, sepsis, cardiovascular shock, severe trauma, acute lung injury, acute respiratory distress syndrome, acute cholecystitis, severe burns, pneumonia, extensive surgical procedures, ischemic bowel disease, severe acute hepatic disease, severe acute hepatic encephalopathy or acute renal failure.

Accordingly, the invention is further directed to methods of treatment of a condition or disorder mediated by KMO, which method comprises administering to a patient in need thereof a therapeutically effective amount of a compound of formula (I) or a pharmaceutically acceptable salt thereof.

The invention is further directed to a pharmaceutical composition comprising a therapeutically effective amount of a compound of formula (I) or a pharmaceutically acceptable salt thereof and a pharmaceutically acceptable excipient.

The invention is further directed to a compound of formula (I) or a pharmaceutically acceptable salt thereof for use in therapy.

The invention is further directed to the use of a compound of formula (I) or a pharmaceutically acceptable salt thereof in the manufacture of a medicament for the treatment of a condition or disorder mediated by KMO.

DETAILED DESCRIPTION OF THE INVENTION

The present invention relates to methods and/or uses for treating pancreatitis, kidney diseases and other various disorders as described herein, for conditions or disorders mediated by KMO inhibitors, which comprises administering 6-chlorobenzoxazine compounds of Formula (I) or pharmaceutically acceptable salts or pharmaceutical compositions thereof.

Compounds

In a first aspect, there are provided compounds of formula (I):

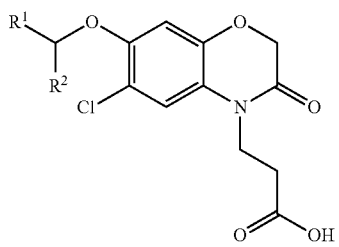

wherein:
$R^1$ is heteroaryl optionally substituted by methyl, ethyl, halo or =O; and
$R^2$ is H, methyl or ethyl.
or a salt thereof.

In one embodiment, $R^1$ is a 5-membered heteroaryl comprising one nitrogen atom or one oxygen atom and further comprising a nitrogen atom, or a 6-membered heteroaryl comprising one, two or three nitrogen atoms, wherein said heteroaryl is optionally substituted by methyl, ethyl, halo or =O.

In one embodiment, $R^1$ is selected from the list consisting of oxazolyl, pyridinyl, pyrimidinyl, pyridazinyl, and imidazolyl, wherein the oxazolyl, pyridinyl, pyrimidinyl, and pyridazinyl may be optionally substituted by methyl, ethyl, chloro or fluoro.

In one embodiment, $R^1$ is selected from the list consisting of oxazolyl (optionally substituted by methyl), pyridinyl (optionally substituted by methyl, ethyl, chloro or fluoro), pyrimidinyl (optionally substituted by methyl or chloro), pyridazinyl (optionally substituted by methyl or chloro) and imidazolyl.

In one embodiment, $R^1$ is selected from the list consisting of pyridin-2-yl, 6-methylpyridazin-3-yl, 5-methylpyrimidin-2-yl, pyrimidin-2-yl, imidazol-2-yl, 6-chloropyridazin-3-yl, pyridazin-3-yl, 5-methylpyridin-2-yl, 5-chloropyrimidin-2-yl, 2-methyloxazol-5-yl, oxazol-2-yl, 5-chloropyridin-2-yl, 5-ethylpyridin-2-yl, and 5-fluoropyridin-2-yl.

In one embodiment, $R^1$ is pyridinyl optionally substituted by methyl, ethyl, chloro or fluoro.

In one embodiment, $R^1$ is 2-pyridinyl optionally substituted by methyl, ethyl, chloro or fluoro.

In one embodiment $R^1$ is 5-chloropyridin-2-yl.

In one embodiment, $R^2$ is methyl.

In one embodiment, $R^2$ is ethyl.

In one embodiment, $R^1$ is 5-chloropyridin-2-yl and $R^2$ is ethyl.

In one embodiment, the compound of formula (I) is selected from the list consisting of:

(3-(6-chloro-7-(1-(5-chloropyridin-2-yl)propoxy)-3-oxo-2H-benzo[b][1,4]oxazin-4(3H)-yl)propanoic acid;

3-{6-chloro-3-oxo-7-[1-(pyridin-2-yl)ethoxy]-3,4-dihydro-2H-1,4-benzoxazin-4-yl}propanoic acid;

3-{6-chloro-7-[1-(2-methyl-1,3-oxazol-5-yl)ethoxy]-3-oxo-3,4-dihydro-2H-1,4-benzoxazin-4-yl}propanoic acid;

3-{6-chloro-7-[1-(1,3-oxazol-2-yl)ethoxy]-3-oxo-3,4-dihydro-2H-1,4-benzoxazin-4-yl}propanoic acid;

3-{6-chloro-7-[1-(1H-imidazol-2-yl)ethoxy]-3-oxo-3,4-dihydro-2H-1,4-benzoxazin-4-yl}propanoic acid;

3-{6-chloro-3-oxo-7-[1-(pyrimidin-2-yl)ethoxy]-3,4-dihydro-2H-1,4-benzoxazin-4-yl}propanoic acid;

3-[6-chloro-3-oxo-7-(pyridin-2-ylmethoxy)-3,4-dihydro-2H-1,4-benzoxazin-4-yl]propanoic acid;

3-{6-chloro-7-[1-(5-methylpyridin-2-yl)ethoxy]-3-oxo-3,4-dihydro-2H-1,4-benzoxazin-4-yl}propanoic acid;

3-{6-chloro-7-[1-(5-chloropyridin-2-yl)ethoxy]-3-oxo-3,4-dihydro-2H-1,4-benzoxazin-4-yl}propanoic acid;

3-{6-chloro-7-[1-(5-fluoropyridin-2-yl)ethoxy]-3-oxo-3,4-dihydro-2H-1,4-benzoxazin-4-yl}propanoic acid;

3-{6-chloro-3-oxo-7-[1-(pyridazin-3-yl)ethoxy]-3,4-dihydro-2H-1,4-benzoxazin-4-yl}propanoic acid;

3-{6-chloro-7-[(6-methylpyridazin-3-yl)methoxy]-3-oxo-3,4-dihydro-2H-1,4-benzoxazin-4-yl}propanoic acid;

3-{6-chloro-7-[1-(6-methylpyridazin-3-yl)ethoxy]-3-oxo-3,4-dihydro-2H-1,4-benzoxazin-4-yl}propanoic acid;

3-{6-chloro-7-[1-(5-methylpyridin-2-yl)propoxy]-3-oxo-3,4-dihydro-2H-1,4-benzoxazin-4-yl}propanoic acid;

3-{6-chloro-3-oxo-7-[1-(pyridin-2-yl)propoxy]-3,4-dihydro-2H-1,4-benzoxazin-4-yl}propanoic acid;

3-{6-chloro-7-[(5-chloropyridin-2-ylmethoxy]-3-oxo-3,4-dihydro-2H-1,4-benzoxazin-4-yl}propanoic acid;

3-{6-chloro-7-[(5-methylpyridin-2-yl)methoxy]-3-oxo-3,4-dihydro-2H-1,4-benzoxazin-4-yl}propanoic acid;

3-{6-chloro-7-[1-(5-ethylpyridin-2-yl)ethoxy]-3-oxo-3,4-dihydro-2H-1,4-benzoxazin-4-yl}propanoic acid;

3-{6-chloro-3-oxo-7-[1-(pyrimidin-2-yl)propoxy]-3,4-dihydro-2H-1,4-benzoxazin-4-yl}propanoic acid;

3-{6-chloro-7-[1-(5-methylpyrimidin-2-yl)propoxy]-3-oxo-3,4-dihydro-2H-1,4-benzoxazin-4-yl}propanoic acid;

3-{6-chloro-7-[1-(5-chloropyrimidin-2-yl)propoxy]-3-oxo-3,4-dihydro-2H-1,4-benzoxazin-4-yl}propanoic acid;

3-{6-chloro-3-oxo-7-[1-(pyridazin-3-yl)propoxy]-3,4-dihydro-2H-1,4-benzoxazin-4-yl}propanoic acid; and 3-{6-chloro-7-[1-(6-methylpyridazin-3-yl)propoxy]-3-oxo-3,4-dihydro-2H-1,4-benzoxazin-4-yl}propanoic acid;

or a pharmaceutically acceptable salt thereof.

In one embodiment, the compound of formula (I) is selected from the list consisting of:

(R)-3-(6-chloro-7-(1-(5-chloropyridin-2-yl)propoxy)-3-oxo-2H-benzo[b][1,4]oxazin-4(3H)-yl)propanoic acid;

3-{6-chloro-3-oxo-7-[(1R)-1-(pyridin-2-yl)ethoxy]-3,4-dihydro-2H-1,4-benzoxazin-4-yl}propanoic acid;

3-{6-chloro-7-[1-(2-methyl-1,3-oxazol-5-yl)ethoxy]-3-oxo-3,4-dihydro-2H-1,4-benzoxazin-4-yl}propanoic acid;

(R)-3-{6-chloro-7-[1-(1,3-oxazol-2-yl)ethoxy]-3-oxo-3,4-dihydro-2H-1,4-benzoxazin-4-yl}propanoic acid;

(S)-3-{6-chloro-7-[1-(1,3-oxazol-2-yl)ethoxy]-3-oxo-3,4-dihydro-2H-1,4-benzoxazin-4-yl}propanoic acid;

3-{6-chloro-7-[1-(1H-imidazol-2-yl)ethoxy]-3-oxo-3,4-dihydro-2H-1,4-benzoxazin-4-yl}propanoic acid;

(R)-3-{6-chloro-3-oxo-7-[1-(pyrimidin-2-yl)ethoxy]-3,4-dihydro-2H-1,4-benzoxazin-4-yl}propanoic acid;

(S)-3-{6-chloro-3-oxo-7-[1-(pyrimidin-2-yl)ethoxy]-3,4-dihydro-2H-1,4-benzoxazin-4-yl}propanoic acid;

3-[6-chloro-3-oxo-7-(pyridin-2-ylmethoxy)-3,4-dihydro-2H-1,4-benzoxazin-4-yl]propanoic acid;

3-{6-chloro-7-[(1R)-1-(5-methylpyridin-2-yl)ethoxy]-3-oxo-3,4-dihydro-2H-1,4-benzoxazin-4-yl}propanoic acid;

3-{6-chloro-7-[(1R)-1-(5-chloropyridin-2-yl)ethoxy]-3-oxo-3,4-dihydro-2H-1,4-benzoxazin-4-yl}propanoic acid;

3-{6-chloro-7-[(1R)-1-(5-fluoropyridin-2-yl)ethoxy]-3-oxo-3,4-dihydro-2H-1,4-benzoxazin-4-yl}propanoic acid;

3-{6-chloro-3-oxo-7-[(1R)-1-(pyridazin-3-yl)ethoxy]-3,4-dihydro-2H-1,4-benzoxazin-4-yl}propanoic acid;

3-{6-chloro-7-[(6-methylpyridazin-3-yl)methoxy]-3-oxo-3,4-dihydro-2H-1,4-benzoxazin-4-yl}propanoic acid;

3-{6-chloro-7-[(1R)-1-(6-methylpyridazin-3-yl)ethoxy]-3-oxo-3,4-dihydro-2H-1,4-benzoxazin-4-yl}propanoic acid;

3-{6-chloro-7-[(1R)-1-(5-methylpyridin-2-yl)propoxy]-3-oxo-3,4-dihydro-2H-1,4-benzoxazin-4-yl}propanoic acid;

3-{6-chloro-3-oxo-7-[(1R)-1-(pyridin-2-yl)propoxy]-3,4-dihydro-2H-1,4-benzoxazin-4-yl}propanoic acid;

3-{6-chloro-7-[(5-chloropyridin-2-ylmethoxy)-3-oxo-3,4-dihydro-2H-1,4-benzoxazin-4-yl}propanoic acid;

3-{6-chloro-7-[(5-methylpyridin-2-yl)methoxy]-3-oxo-3,4-dihydro-2H-1,4-benzoxazin-4-yl}propanoic acid;

3-{6-chloro-7-[(1R)-1-(5-ethylpyridin-2-yl)ethoxy]-3-oxo-3,4-dihydro-2H-1,4-benzoxazin-4-yl}propanoic acid;

(R)-3-{6-chloro-3-oxo-7-[1-(pyrimidin-2-yl)propoxy]-3,4-dihydro-2H-1,4-benzoxazin-4-yl}propanoic acid;

(S)-3-{6-chloro-3-oxo-7-[1-(pyrimidin-2-yl)propoxy]-3,4-dihydro-2H-1,4-benzoxazin-4-yl}propanoic acid;

(R)-3-{6-chloro-7-[1-(5-methylpyrimidin-2-yl)propoxy]-3-oxo-3,4-dihydro-2H-1,4-benzoxazin-4-yl}propanoic acid;

(S)-3-{6-chloro-7-[1-(5-methylpyrimidin-2-yl)propoxy]-3-oxo-3,4-dihydro-2H-1,4-benzoxazin-4-yl}propanoic acid;

(R)-3-{6-chloro-7-[1-(5-chloropyrimidin-2-yl)propoxy]-3-oxo-3,4-dihydro-2H-1,4-benzoxazin-4-yl}propanoic acid;

(S)-3-{6-chloro-7-[1-(5-chloropyrimidin-2-yl)propoxy]-3-oxo-3,4-dihydro-2H-1,4-benzoxazin-4-yl}propanoic acid;

(R)-3-{6-chloro-3-oxo-7-[1-(pyridazin-3-yl)propoxy]-3,4-dihydro-2H-1,4-benzoxazin-4-yl}propanoic acid;

(S)-3-{6-chloro-3-oxo-7-[1-(pyridazin-3-yl)propoxy]-3,4-dihydro-2H-1,4-benzoxazin-4-yl}propanoic acid;

(R)-3-{6-chloro-7-[1-(6-methylpyridazin-3-yl)propoxy]-3-oxo-3,4-dihydro-2H-1,4-benzoxazin-4-yl}propanoic acid; and (S)-3-{6-chloro-7-[1-(6-methylpyridazin-3-yl)propoxy]-3-oxo-3,4-dihydro-2H-1,4-benzoxazin-4-yl}propanoic acid;

or a pharmaceutically acceptable salt thereof.

In one embodiment, the compound of the invention is selected from the list consisting of:

(R)-3-(6-chloro-7-(1-(5-chloropyridin-2-yl)propoxy)-3-oxo-2H-benzo[b][1,4]oxazin-4(3H)-yl)propanoic acid;

2-amino-2-(hydroxymethyl)propane-1,3-diol; 3-{6-chloro-3-oxo-7-[(1R)-1-(pyridin-2-yl)ethoxy]-3,4-dihydro-2H-1,4-benzoxazin-4-yl}propanoic acid;

3-{6-chloro-3-oxo-7-[(1R)-1-(pyridin-2-yl)ethoxy]-3,4-dihydro-2H-1,4-benzoxazin-4-yl}propanoic acid;

3-{6-chloro-3-oxo-7-[(1R)-1-(pyridin-2-yl)ethoxy]-3,4-dihydro-2H-1,4-benzoxazin-4-yl}propanoic acid hydrochloride;

(2S)-2-amino-5-carbamimidamidopentanoic acid; 3-{6-chloro-3-oxo-7-[(1R)-1-(pyridin-2-yl)ethoxy]-3,4-dihydro-2H-1,4-benzoxazin-4-yl}propanoic acid;

(2S)-2,6-diaminohexanoic acid; 3-{6-chloro-3-oxo-7-[(1R)-1-(pyridin-2-yl)ethoxy]-3,4-dihydro-2H-1,4-benzoxazin-4-yl}propanoic acid;

3-{6-chloro-3-oxo-7-[(1R)-1-(pyridin-2-yl)ethoxy]-3,4-dihydro-2H-1,4-benzoxazin-4-yl}propanoic acid; benzyl[2-(benzylamino)ethyl]amine;

3-{6-chloro-3-oxo-7-[(1R)-1-(pyridin-2-yl)ethoxy]-3,4-dihydro-2H-1,4-benzoxazin-4-yl}propanoic acid; sulfuric acid;

3-{6-chloro-3-oxo-7-[(1R)-1-(pyridin-2-yl)ethoxy]-3,4-dihydro-2H-1,4-benzoxazin-4-yl}propanoic acid; methanesulfonic acid;

3-{6-chloro-3-oxo-7-[(1R)-1-(pyridin-2-yl)ethoxy]-3,4-dihydro-2H-1,4-benzoxazin-4-yl}propanoic acid; 4-methylbenzene-1-sulfonic acid;

3-{6-chloro-3-oxo-7-[(1R)-1-(pyridin-2-yl)ethoxy]-3,4-dihydro-2H-1,4-benzoxazin-4-yl}propanoic acid; benzyl(2-phenylethyl)amine;

3-{6-chloro-3-oxo-7-[(1R)-1-(pyridin-2-yl)ethoxy]-3,4-dihydro-2H-1,4-benzoxazin-4-yl}propanoic acid; bis(2-aminoethyl)amine;

(2R,3R,4R,5S)-6-(methylamino)hexane-1,2,3,4,5-pentol; 3-{6-chloro-3-oxo-7-[(1R)-1-(pyridin-2-yl)ethoxy]-3,4-dihydro-2H-1,4-benzoxazin-4-yl}propanoic acid;

sodium 3-{6-chloro-3-oxo-7-[(1R)-1-(pyridin-2-yl)ethoxy]-3,4-dihydro-2H-1,4-benzoxazin-4-yl}propanoate;

2-amino-2-(hydroxymethyl)propane-1,3-diol; 3-{6-chloro-7-[1-(2-methyl-1,3-oxazol-5-yl)ethoxy]-3-oxo-3,4-dihydro-2H-1,4-benzoxazin-4-yl}propanoic acid;

2-amino-2-(hydroxymethyl)propane-1,3-diol; (R)-3-{6-chloro-7-[1-(1,3-oxazol-2-yl)ethoxy]-3-oxo-3,4-dihydro-2H-1,4-benzoxazin-4-yl}propanoic acid;

2-amino-2-(hydroxymethyl)propane-1,3-diol; (S)-3-{6-chloro-7-[1-(1,3-oxazol-2-yl)ethoxy]-3-oxo-3,4-dihydro-2H-1,4-benzoxazin-4-yl}propanoic acid;

2-amino-2-(hydroxymethyl)propane-1,3-diol; 3-{6-chloro-7-[1-(1H-imidazol-2-yl)ethoxy]-3-oxo-3,4-dihydro-2H-1,4-benzoxazin-4-yl}propanoic acid;

2-amino-2-(hydroxymethyl)propane-1,3-diol; (R)-3-{6-chloro-3-oxo-7-[1-(pyrimidin-2-yl)ethoxy]-3,4-dihydro-2H-1,4-benzoxazin-4-yl}propanoic acid;

2-amino-2-(hydroxymethyl)propane-1,3-diol; (S)-3-{6-chloro-3-oxo-7-[1-(pyrimidin-2-yl)ethoxy]-3,4-dihydro-2H-1,4-benzoxazin-4-yl}propanoic acid;

3-[6-chloro-3-oxo-7-(pyridin-2-ylmethoxy)-3,4-dihydro-2H-1,4-benzoxazin-4-yl]propanoic acid;

3-{6-chloro-7-[(1R)-1-(5-methylpyridin-2-yl)ethoxy]-3-oxo-3,4-dihydro-2H-1,4-benzoxazin-4-yl}propanoic acid;

3-{6-chloro-7-[(1R)-1-(5-chloropyridin-2-yl)ethoxy]-3-oxo-3,4-dihydro-2H-1,4-benzoxazin-4-yl}propanoic acid;
3-{6-chloro-7-[(1R)-1-(5-fluoropyridin-2-yl)ethoxy]-3-oxo-3,4-dihydro-2H-1,4-benzoxazin-4-yl}propanoic acid;
3-{6-chloro-3-oxo-7-[(1R)-1-(pyridazin-3-yl)ethoxy]-3,4-dihydro-2H-1,4-benzoxazin-4-yl}propanoic acid;
3-{6-chloro-7-[(6-methylpyridazin-3-yl)methoxy]-3-oxo-3,4-dihydro-2H-1,4-benzoxazin-4-yl}propanoic acid;
3-{6-chloro-7-[(1R)-1-(6-methylpyridazin-3-yl)ethoxy]-3-oxo-3,4-dihydro-2H-1,4-benzoxazin-4-yl}propanoic acid;
3-{6-chloro-7-[(1R)-1-(5-methylpyridin-2-yl)propoxy]-3-oxo-3,4-dihydro-2H-1,4-benzoxazin-4-yl}propanoic acid;
3-{6-chloro-3-oxo-7-[(1R)-1-(pyridin-2-yl)propoxy]-3,4-dihydro-2H-1,4-benzoxazin-4-yl}propanoic acid;
3-{6-chloro-7-[(5-chloropyridin-2-ylmethoxy)]-3-oxo-3,4-dihydro-2H-1,4-benzoxazin-4-yl}propanoic acid;
3-{6-chloro-7-[(5-methylpyridin-2-yl)methoxy]-3-oxo-3,4-dihydro-2H-1,4-benzoxazin-4-yl}propanoic acid;
3-{6-chloro-7-[(1R)-1-(5-ethylpyridin-2-yl)ethoxy]-3-oxo-3,4-dihydro-2H-1,4-benzoxazin-4-yl}propanoic acid;
(R)-3-{6-chloro-3-oxo-7-[1-(pyrimidin-2-yl)propoxy]-3,4-dihydro-2H-1,4-benzoxazin-4-yl}propanoic acid;
(S)-3-{6-chloro-3-oxo-7-[1-(pyrimidin-2-yl)propoxy]-3,4-dihydro-2H-1,4-benzoxazin-4-yl}propanoic acid;
(R)-3-{6-chloro-7-[1-(5-methylpyrimidin-2-yl)propoxy]-3-oxo-3,4-dihydro-2H-1,4-benzoxazin-4-yl}propanoic acid;
(S)-3-{6-chloro-7-[1-(5-methylpyrimidin-2-yl)propoxy]-3-oxo-3,4-dihydro-2H-1,4-benzoxazin-4-yl}propanoic acid;
(R)-3-{6-chloro-7-[1-(5-chloropyrimidin-2-yl)propoxy]-3-oxo-3,4-dihydro-2H-1,4-benzoxazin-4-yl}propanoic acid;
(S)-3-{6-chloro-7-[1-(5-chloropyrimidin-2-yl)propoxy]-3-oxo-3,4-dihydro-2H-1,4-benzoxazin-4-yl}propanoic acid;
(R)-3-{6-chloro-3-oxo-7-[1-(pyridazin-3-yl)propoxy]-3,4-dihydro-2H-1,4-benzoxazin-4-yl}propanoic acid;
(S)-3-{6-chloro-3-oxo-7-[1-(pyridazin-3-yl)propoxy]-3,4-dihydro-2H-1,4-benzoxazin-4-yl}propanoic acid;
(R)-3-{6-chloro-7-[1-(6-methylpyridazin-3-yl)propoxy]-3-oxo-3,4-dihydro-2H-1,4-benzoxazin-4-yl}propanoic acid; and
(S)-3-{6-chloro-7-[1-(6-methylpyridazin-3-yl)propoxy]-3-oxo-3,4-dihydro-2H-1,4-benzoxazin-4-yl}propanoic acid.

In one embodiment, the compound of formula (I) is: 3-(6-chloro-7-(1-(5-chloropyridin-2-yl)propoxy)-3-oxo-2H-benzo[b][1,4]oxazin-4(3H)-yl)propanoic acid or a pharmaceutically acceptable salt thereof.

In one embodiment, the compound of formula (I) is: 3-(6-chloro-7-(1-(5-chloropyridin-2-yl)propoxy)-3-oxo-2H-benzo[b][1,4]oxazin-4(3H)-yl)propanoic acid or a pharmaceutically acceptable salt thereof.

In one embodiment, the compound of formula (I) is: 3-(6-chloro-7-(1-(5-chloropyridin-2-yl)propoxy)-3-oxo-2H-benzo[b][1,4]oxazin-4(3H)-yl)propanoic acid.

In one embodiment, the compound of formula (I) is: 3-(6-chloro-7-(1-(5-chloropyridin-2-yl)propoxy)-3-oxo-2H-benzo[b][1,4]oxazin-4(3H)-yl)propanoic acid in the form of a pharmaceutically acceptable salt.

In one embodiment, the compound of formula (I) is: (R)-3-(6-chloro-7-(1-(5-chloropyridin-2-yl)propoxy)-3-oxo-2H-benzo[b][1,4]oxazin-4(3H)-yl)propanoic acid or a pharmaceutically acceptable salt thereof.

In one embodiment, the compound of formula (I) is: (R)-3-(6-chloro-7-(1-(5-chloropyridin-2-yl)propoxy)-3-oxo-2H-benzo[b][1,4]oxazin-4(3H)-yl)propanoic acid or a pharmaceutically acceptable salt thereof.

In one embodiment, the compound of formula (I) is: (R)-3-(6-chloro-7-(1-(5-chloropyridin-2-yl)propoxy)-3-oxo-2H-benzo[b][1,4]oxazin-4(3H)-yl)propanoic acid.

In one embodiment, the compound of formula (I) is: (R)-3-(6-chloro-7-(1-(5-chloropyridin-2-yl)propoxy)-3-oxo-2H-benzo[b][1,4]oxazin-4(3H)-yl)propanoic acid in the form of a pharmaceutically acceptable salt.

Terms and Definitions

Compounds of formula (I) and salts thereof are referred to hereinafter as "Compounds of the invention".

The term "halogen" or "halo" as used herein refers to fluorine (F), chlorine (Cl), bromine (Br), or iodine (I). Examples of suitable halogens are fluorine and chlorine.

The term "heteroaryl" as used herein refers to a 5- or 6-membered aromatic ring which comprises one or more (e.g. 1, 2 or 3) heteroatoms independently selected from oxygen, nitrogen or sulphur. For example, when "heteroaryl" represents a 5-membered ring, the ring contains a heteroatom selected from oxygen, nitrogen or sulphur and may optionally further contain one, two or three nitrogen atoms. When "heteroaryl" represents a 6-membered ring, the ring may contain one, two or three nitrogen atoms. Examples of such 5- or 6-membered heteroaryl rings include, but are not limited to, pyrrolyl, triazolyl, thiadiazolyl, tetrazolyl, imidazolyl, pyrazolyl, isothiazolyl, thiazolyl, isoxazolyl, oxazolyl, oxadiazolyl, furazanyl, furanyl, thienyl, pyridyl, pyrimidinyl, pyrazinyl, pyridazinyl and triazinyl.

'Enantiomeric excess' (ee) is the excess of one enantiomer over the other expressed as a percentage. In a racemic modification, since both enantiomers are present in equal amounts, the enantiomeric excess is zero (0% ee). However, if one enantiomer were enriched such that it constitutes 95% of the product, then the enantiomeric excess would be 90% ee (the amount of the enriched enantiomer, 95%, minus the amount of the other enantiomer, 5%).

'Enantiomerically enriched' refers to products whose enantiomeric excess (ee) is greater than zero. For example, 'enantiomerically enriched' refers to products whose enantiomeric excess is greater than 50% ee, greater than 75% ee, and greater than 90% ee.

'Enantiomerically pure' refers to products whose enantiomeric excess is 99% or greater 'Optionally substituted' means substituted or unsubstituted.

The compounds of the invention are capable of forming base addition salts. Such salts can be formed by reaction with the appropriate base, optionally in a suitable solvent such as an organic solvent, to give the salt which can be isolated by crystallisation and filtration.

The compounds of the invention are also capable of forming acid addition salts. Such salts can be formed by reaction with the appropriate acid, optionally in a suitable solvent such as an organic solvent, to give the salt which can be isolated by crystallisation and filtration.

It is to be understood that the references herein to compounds of formula (I) and salts thereof covers the compounds of formula (I) as free bases, free acids, or as salts thereof, for example as pharmaceutically acceptable salts thereof. Thus in one embodiment, the invention is directed to compounds of formula (I) as the free acid. In another embodiment, the invention is directed to compounds of formula (I) as the free base. In another embodiment, the invention is directed to compounds of formula (I) and salts thereof. In a further embodiment, the invention is directed to compounds of formula (I) and pharmaceutically acceptable salts thereof.

Because of their potential use in medicine, it will be appreciated that for use in medicine the salts of the compounds of the invention should be pharmaceutically acceptable. Pharmaceutically acceptable salts will be apparent to those skilled in the art and include those described in Berge, J. Pharm. Sci., 1977, 66, 1-19. Pharmaceutically acceptable base addition salts include, but are not limited to, ammonium salts, alkali metal salts such as those of sodium and potassium, alkaline earth metal salts such as those of calcium and magnesium and salts with organic bases, including salts of primary, secondary and tertiary amines, such as t-butylamine, cyclohexylamine, dimethylamine, trimethylamine, diethyltriamine, 2-amino-2-(hydroxymethyl)-1,3-propanediol (TRIS), ethanolamine, choline and N-methyl-D-glucamine. Pharmaceutically acceptable acid addition salts include, but are not limited to, hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), napthalene-2-sulfonate, ethanedisulfonate, and 2,5-dihydroxybenzoate.

In one embodiment, the salt is a pharmaceutically acceptable salt.

Certain compounds of the invention may contain an asymmetric centre (also referred to as a chiral centre) and may, therefore, exist as individual enantiomers, or as mixtures thereof. Where the stereochemistry of a chiral centre present in formula (I), or in any chemical structure illustrated herein, is not specified, the structure is intended to encompass any stereoisomer and all mixtures thereof. Thus, compounds according to formula (I) containing one or more chiral centres may be used as racemic modifications including racemic mixtures and racemates, enantiomerically-enriched mixtures, or as enantiomerically-pure individual stereoisomers. It will be understood that the invention encompasses all geometric and optical isomers of these compounds and the mixtures thereof including racemates. The invention also extends to any tautomeric forms and mixtures thereof.

Individual stereoisomers of a compound according to formula (I) which contain an asymmetric centre may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. It will be appreciated that where the desired stereoisomer is converted into another chemical entity by one of the separation procedures described above, a further step is required to liberate the desired form. Alternatively, specific stereoisomers may be synthesised by asymmetric synthesis using optically active reagents, substrates, catalysts or solvents, or by converting one enantiomer to the other by asymmetric transformation.

In one aspect, there is provided a compound of formula (I) wherein $R_2$ is not H, and wherein the (R) enantiomer is present in greater than 90% enantiomeric excess ("ee").

In one embodiment, the (R) enantiomer is present in greater than 95% ee.

In one embodiment, the (R) enantiomer is present in greater than 99% ee.

The invention includes within its scope all possible stoichiometric and non-stoichiometric forms of the salts of the compounds of formula (I).

Certain compounds of the invention may exist in the form of solvates. As used herein, the term "solvate" refers to a complex of variable stoichiometry formed by a solute (in this invention, a compound of formula (I) or a salt thereof) and a solvent. Such solvents for the purpose of the invention may not interfere with the biological activity of the solute. Examples of suitable solvents include water, methanol, ethanol and acetic acid. If the solvent used is water, the solvate may be referred to as a hydrate.

It will be further appreciated that certain compounds of the invention that exist in crystalline form, including the various solvates thereof, may exhibit polymorphism (i.e. the capacity to occur in different crystalline structures). These different crystalline forms are typically known as 'polymorphs'. The invention includes such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. It will be appreciated that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

Compounds of formula (I) and salts thereof may be isotopically-labelled and as such are identical to compounds of the invention, but for one or more atoms having been replaced by an atom having an atomic mass or mass number different from the atomic mass or mass number most commonly found in nature. Examples of isotopes that can be incorporated into compounds of the invention are isotopes of hydrogen, carbon, nitrogen, fluorine, such as $^{3}H$, $^{11}C$, $^{14}C$ and $^{18}F$. Such isotopically-labelled compounds are useful in drug and/or substrate tissue distribution assays. For example, $^{11}C$ and $^{18}F$ isotopes are particularly useful in PET (positron emission tomography). PET is useful in brain imaging. Isotopically labelled compounds of the invention can generally be prepared by carrying out the procedures disclosed below, by substituting a readily available isotopically labelled reagent for a non-isotopically labelled reagent.

The invention also includes various deuterated forms of the compounds of Formula (I) or a pharmaceutically acceptable salt thereof as defined herein, or corresponding pharmaceutical compositions containing such compounds, respectively. Each available hydrogen atom attached to a carbon atom may be independently replaced with a deuterium atom. A person of ordinary skill in the art will know how to synthesize deuterated forms of the compounds of the present invention, respectively, or a pharmaceutically acceptable salt thereof or corresponding pharmaceutical compositions containing such compounds, of the present invention. For example, deuterated materials, such as alkyl groups may be prepared by conventional techniques (see for example: methyl-$d_3$-amine available from Aldrich Chemical Co., Milwaukee, Wis., Cat. No. 489, 689-2).

Abbreviations conc. concentrated
DCM dichloromethane
DEAD diethylazodicarboxylate
DMF N,N-dimethylformamide
DMSO dimethylsulphoxide
EDCI 3-ethyl-1(N,N-dimethyl)aminopropylcarbodiimide
ESI electrospray ionisation
h hour(s)
HOBT 1-hydroxybenzotriazole
HPLC high performance liquid chromatography
LCMS liquid chromatography-mass spectrometry
MeCN acetonitrile
min minutes
mL millilitre
Ms/mesyl methanesulphonyl
NBS N-bromosuccinamide
NMR nuclear magnetic resonance
Pd(dppf)Cl$_2$ [1,1'-bis(diphenylphosphino)ferrocene]dichloro palladium II
R-CBS (R)-3,3-diphenyl-1-methylpyrrolidino[1,2-c]-1,3,2-oxazaborole
RT room temperature
Rt retention time
SFC supercritical fluid chromatography
THF tetrahydrofuran
TFA trifluoroacetic acid
TRIS 2-amino-2-(hydroxymethyl)-1,3-propanediol
Compound Preparation Compounds of formula (I) (wherein $R^1$ and $R^2$ are as hereinbefore defined) may be synthesised substantially according to Reaction Scheme 1 from the corresponding ester of formula (II) (wherein R is, for example, methyl or ethyl) by acid mediated hydrolysis or saponification. The ester of formula (II) may be obtained by treatment of alkyl 3-(6-chloro-7-hydroxy-3-oxo-2H-benzo[b][1,4]oxazin-4(3H)-yl)propanoate with an alcohol of formula (IV) under Mitsonobu conditions.

Reaction Scheme 1

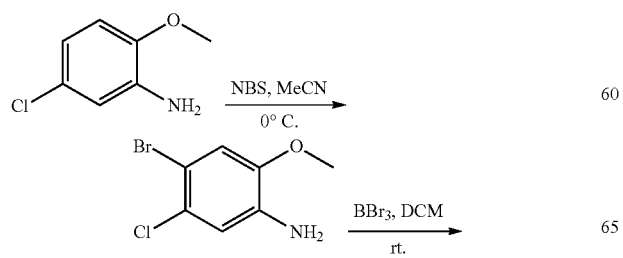

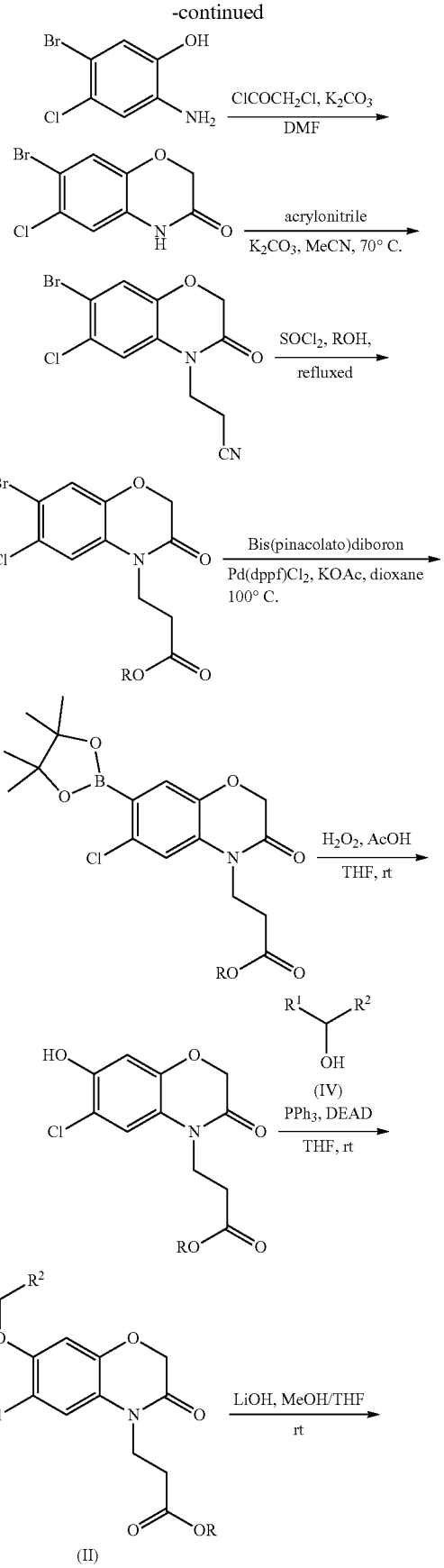

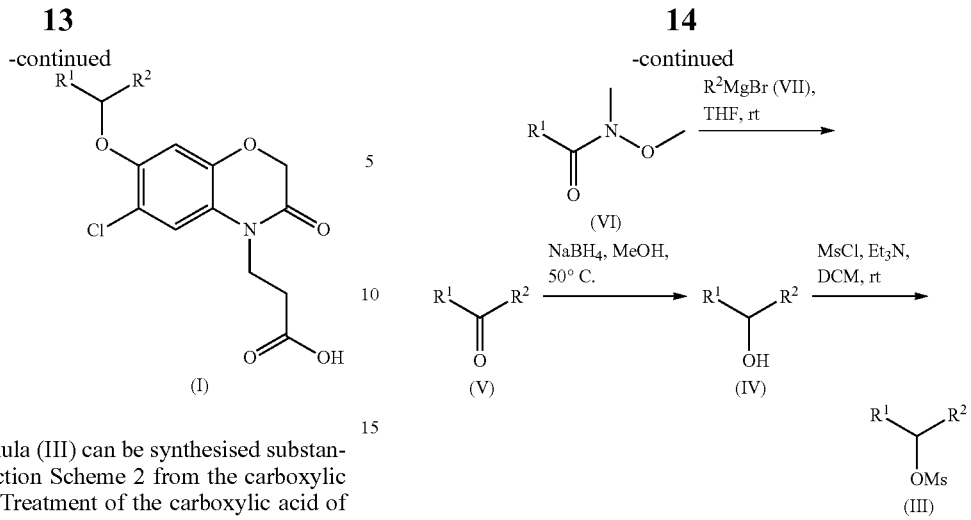

The mesylate of formula (III) can be synthesised substantially according to Reaction Scheme 2 from the carboxylic acid of formula (VIII). Treatment of the carboxylic acid of formula (VIII) with N,O-dimethylhydroxylamine in the presence of suitable coupling agents, for instance HOBT and EDCI, to afford the Weinreb amide of formula (VII), followed by treatment with the Grignard reagent of formula (VI) affords the ketone of formula (V). Reduction of the ketone of formula (V) with a suitable reducing agent, for instance sodium borohydride affords the achiral alcohol (IV), which may be optionally activated, for instance as the mesylate of formula (III) by introduction of a suitable activating group, for instance mesylate, by treatment with an activating agent, for instance by treatment with mesyl chloride (MsCl), in a suitable solvent, for instance dichloromethane (DCM), using a suitable base, for instance triethylamine (Et$_3$N), at a suitable temperature, for instance ambient temperature.

Alternatively, the mesylate of formula (III) may be synthesised substantially according to Reaction Scheme 3, by treatment of the cyano compound of formula (IX) with a Grignard reagent of formula (VII) in a suitable solvent, for instance THF, at a suitable temperature, for instance 0° C., to afford the ketone or aldehyde of formula (V).

Reduction of the aldehyde or ketone of formula (V) under achiral conditions, for instance using sodium borohydride in a suitable solvent, for instance methanol, affords the achiral alcohol of formula (IV).

Reduction of the ketone of formula (V) (R$^2$ is not H) under chiral conditions, for instance using R-CBS ((R)-3,3-diphenyl-1-methylpyrrolidino[1,2-c]-1,3,2-oxazaborole) and borane-dimethylsulphide in a suitable solvent, for instance THF, affords the chiral alcohol (IVA).

The chiral alcohol of formula (IV) or achiral alcohol of formula (IVA) may be optionally activated, for instance as the corresponding mesylate of formula (III) or formula (IIIA) by introduction of a suitable activating group, for instance mesylate, by treatment with an activating agent, for instance by treatment with mesyl chloride (MsCl), in a suitable solvent, for instance dichloromethane (DCM), using a suitable base, for instance triethylamine (Et$_3$N), at a suitable temperature, for instance ambient temperature.

Reaction Scheme 2

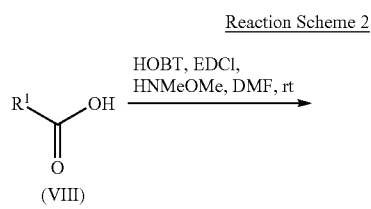

Reaction Scheme 3

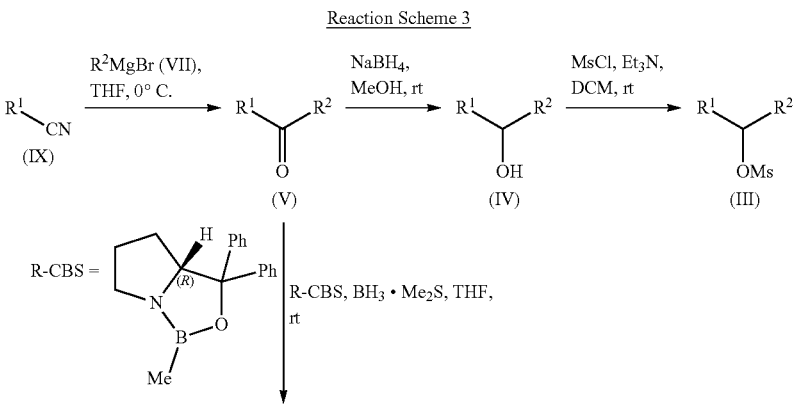

-continued

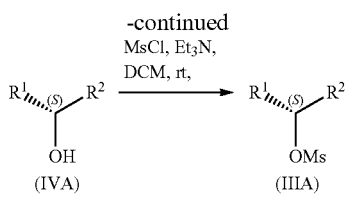

The activated alcohol CH($R^1$)($R^2$)OMs of formula (III) or (IIIA) can be synthesised from the racemic alcohol of formula (IV), obtained from reduction of the aldehyde or ketone of formula (VI), substantially according to Reaction Scheme 4 (to produce racemic activated alcohol of formula (III)) or from the chiral alcohol of formula (IVA) obtained from chiral reduction of the ketone of formula (V) substantially according to Reaction Scheme 5 (to produce substantially chirally pure activated alcohol CH($R^1$)($R^2$)OMs of formula (IIIA))

Reaction Scheme 4

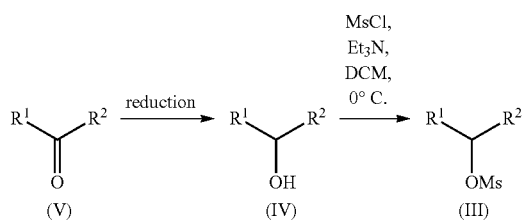

Reaction Scheme 5

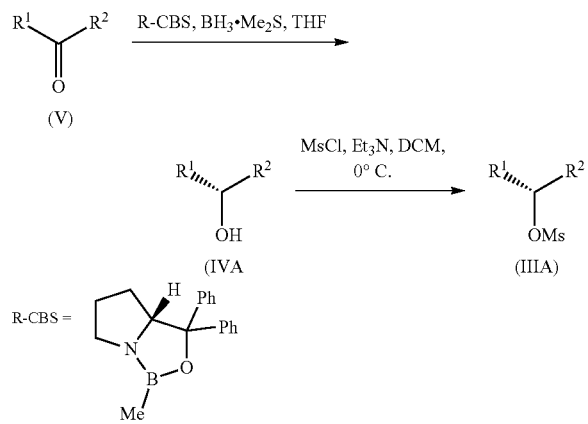

The alkyl ester of formula (II) may also be obtained by treatment of alkyl 3-(6-chloro-7-hydroxy-3-oxo-2H-benzo[b][1,4]oxazin-4(3H)-yl)propanoate with an activated alcohol of formula (III) or (IIIA) under alkylation conditions, in a suitable solvent, for instance acetonitrile, in the presence of a suitable base, for instance potassium carbonate.

It will be appreciated by those skilled in the art that it may be necessary to protect certain reactive substituents during some of the above procedures. Standard protection and deprotection techniques, such as those described in "Greene T. W. Protective groups in organic synthesis, New York, Wiley (1981)", can be used. For example, primary amines can be protected as phthalimide, trifluoroacetyl, benzyl, tert-butyloxycarbonyl, benzyloxycarbonyl or trityl derivatives. Carboxylic acid groups can be protected as esters. Aldehyde or ketone groups can be protected as acetals, ketals, thioacetals or thioketals. Deprotection of such groups is achieved using conventional procedures well known in the art. For example, protecting groups such as tert-butyloxycarbonyl may be removed using an acid such as hydrochloric or trifluroroacetic acid in a suitable solvent such as dichloromethane, diethylether, 1,4-dioxane, isopropanol or mixtures thereof.

For any of the hereinbefore described reactions or processes, conventional methods of heating and cooling may be employed, for example temperature-regulated oil-baths or temperature-regulated hot-blocks, and ice/salt baths or dry ice/acetone baths respectively. Conventional methods of isolation, for example extraction from or into aqueous or non-aqueous solvents may be used. Conventional methods of drying organic solvents, solutions, or extracts, such as shaking with anhydrous magnesium sulfate, or anhydrous sodium sulfate, or passing through a hydrophobic frit, may be employed. Conventional methods of purification, for example crystallisation and chromatography, for example silica chromatography or reverse-phase chromatography, may be used as required. Crystallisation may be performed using conventional solvents such as ethyl acetate, methanol, ethanol, or butanol, or aqueous mixtures thereof. It will be appreciated that specific reaction times and temperatures may typically be determined by reaction-monitoring techniques, for example thin-layer chromatography and LCMS.

General Methods

Unless stated otherwise, starting materials were commercially available. All solvents and commercial reagents were of laboratory grade and were used as received.

Where diasteroisomers are represented and only the relative stereochemistry is referred to, or where an enantiomer is represented and the absolute stereochemistry is unknown, the use of "or1" at the chiral centre denotes that the absolute stereochemistry of the particular compound is unknown, i.e. the compound as drawn may be either the R enantiomer or the S enantiomer. Where the absolute stereochemistry is known and the compound is a single enantiomer, the bold or hashed wedge symbol ( ▬ / ▬▬▬ ) are used as appropriate, without the use of "or1" at the chiral centre.

Analytical Methods

LCMS Conditions

Agilent 1200-6110,

Signal table: Signal A: 214 nm, Signal B: 254 nm;

Column Temperature: 40° C.

Column: HALO C18 4.6*50 mm, 2.7 μm

| Solvents | Gradient | Polarity |
|---|---|---|
| Solvent A: $H_2O$ (0.1% formic acid) | 0.00 min: A: 95.0% B: 5.0% 1.00 min: A: 5.0% B: 95.0% | Positive |

| Solvents | Gradient | Polarity |
|---|---|---|
| Solvent B: CH₃CN | 2.00 min: A: 5.0% B: 95.0% | |
| (0.1% formic acid) | 2.01 min: A: 95.0% B: 5.0% | |
| | 2.50 min: A: 95.0% B: 5.0% | |

The names of the intermediates and examples have been obtained using the compound naming programme within "ChemBioDraw Ultra v12", or alternatively using "ACD Name Pro 6.02".

Intermediate 1: 4-Bromo-5-chloro-2-methoxyaniline

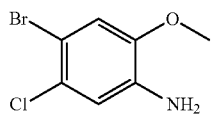

To 5-chloro-2-methoxyaniline (132 g, 0.84 mol) in acetonitrile (1000 mL), N-bromosuccinimide (150 g, 0.84 mol) was added in portions at 0° C. over 1 h. After addition, the mixture was stirred at ambient temperature for 16 h. This reaction was repeated 3 times and the 4 reactions combined. The mixture was poured into ice/water (4 kg×2) and stirred for 1 h. The mixture was basified with solid sodium bicarbonate to between pH7 and 8. The aqueous layer was extracted with ethyl acetate (2L×3), the combined organic layer dried over sodium sulphate, filtered and the solvent was evaporated under vacuum. The residue was purified by column chromatography (silica, 200-300 mesh, 4 Kg, petroleum ether/ethyl acetate 50:1 to remove dibromo by-product, then petroleum ether/ethyl acetate 10:1) to give 4-bromo-5-chloro-2-methoxyaniline as a light-brown solid (380 g).

LCMS: Rt 1.57 min, MH⁺ 236/238.

Intermediate 2: 2-Amino-5-bromo-4-chlorophenol

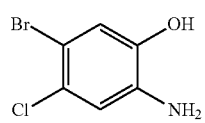

To each of 2 ice/water cooled flasks, containing 4-bromo-5-chloro-2-methoxyaniline (120 g, 507.42 mmol) in DCM (1000 mL) was added boron tribromide (382 g, 1522.26 mmol). After addition, the mixture was warmed to room temperature and stirred for 2 h. The reaction mixtures were poured into ice/water (2L), basified with solid sodium bicarbonate to pH 7 and extracted with ethyl acetate (1000 mL×6). The combined organics were dried over sodium sulphate and the solvent removed to give 2-amino-5-bromo-4-chlorophenol as a brown solid (220 g).

LCMS: Rt 1.35 min, MH⁺ 222/224.

Intermediate 3: 7-Bromo-6-chloro-2H-benzo[b][1,4]oxazin-3(4H)-one

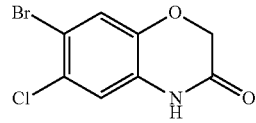

To 2-amino-5-bromo-4-chlorophenol (218 g, 979.9 mmol) in DMF (1000 mL) was added 2-chloroacetyl chloride (121.7 g, 1077.9 mmol) at room temperature and the mixture stirred at this temperature for 3 h. Potassium carbonate (270.5 g, 1959.8 mmol) was added to the mixture, and stirring continued for 16 h. Potassium carbonate (135 g, 979.9 mmol) was added to the mixture and the reaction mixture was stirred at room temperature for a further 16 h. Water (2 L) was added and the product isolated by filtration to afford 7-bromo-6-chloro-2H-benzo[b][1,4]oxazin-3(4H)-one as a brown solid (225 g).

LCMS: Rt 1.56 min, MH⁺ 261.

Intermediate 4: 3-(7-Bromo-6-chloro-3-oxo-2H-benzo[b][1,4]oxazin-4(3H)-yl)propanenitrile

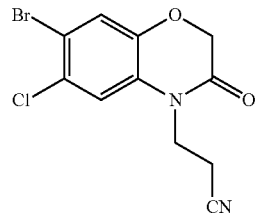 [SMILES: N#CCCN1C(=O)COc2cc(Br)c(Cl)cc21]

To 7-bromo-6-chloro-2H-benzo[b][1,4]oxazin-3(4H)-one (227 g, 865 mmol) in MeCN (1000 mL) were added acrylonitrile (138 g, 2.595 mol) and potassium carbonate (358.11 g, 2.595 mol). After addition, the reaction mixture was stirred at 70° C. for 16 h, the solvent removed and the residue purified by column chromatography (silica:200-300 mesh, 1000 g, petroleum ether/ethyl acetate 5:1) to give 3-(7-bromo-6-chloro-3-oxo-2H-benzo[b][1,4]oxazin-4(3H)-yl)propanenitrile as a brown solid (230 g).

¹H NMR (300 MHz, CDCl₃) δ 7.28 (s, 1H), 7.10 (s, 1H), 4.63 (s, 2H), 4.19 (t, J=7.0 Hz, 2H), 2.78 (t, J=7.1 Hz, 2H).].

Intermediate 5: Methyl 3-(7-bromo-6-chloro-3-oxo-2H-benzo[b][1,4]oxazin-4(3H)-yl)propanoate

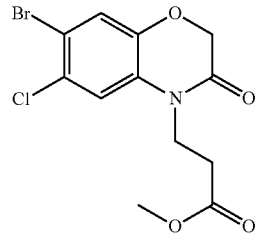 [SMILES: COC(=O)CCN1C(=O)COc2cc(Br)c(Cl)cc21]

To 3-(7-bromo-6-chloro-3-oxo-2H-benzo[b][1,4]oxazin-4(3H)-yl)propanenitrile (100 g, 317 mmol) in methanol (600 mL) was added thionyl chloride (300 mL) at 0° C. After addition, the reaction was heated at 70° C. for 16 h. The solvent was removed and the residue was poured into water (1000 mL), extracted with DCM (800 mL×4), concentrated and purified by column chromatography (silica:200-300 mesh, 800 g, DCM/MeOH 100:1) to give methyl 3-(7-bromo-6-chloro-3-oxo-2H-benzo[b][1,4]oxazin-4(3H)-yl)propanoate as a brown solid (108 g).

LCMS: Rt 1.59 min, MH$^+$ 348/350; $^1$H NMR (300 MHz, CDCl$_3$) δ 7.24 (s, 1H), 7.12 (s, 1H), 4.60 (s, 2H), 4.18 (t, J=6, 2H), 3.71 (s, 3H), 3.65 (s, 1H), 2.70 (t, J=6, 2H).

Intermediate 6: Methyl 3-(6-chloro-3-oxo-7-(4,4,5,5-tetramethyl-1,3,2-dioxaborolan-2-yl)-2H-benzo[b][1,4]oxazin-4(3H)-yl)propanoate

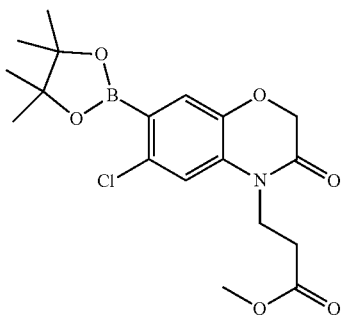 [SMILES: COC(=O)CCN1C(=O)COc2cc(B3OC(C)(C)C(C)(C)O3)c(Cl)cc21]

To methyl 3-(7-bromo-6-chloro-3-oxo-2H-benzo[b][1,4]oxazin-4(3H)-yl)propanoate (108 g, 310 mmol) in 1,4-dioxane (600 mL), was added 4,4,4',4',5,5,5',5'-octamethyl-2,2'-bi(1,3,2-dioxaborolane) (236 g, 930 mmol), [1,1'-bis(diphenylphosphino)ferrocene] dichloro palladium(II) (11.34 g, 15.5 mmol), potassium acetate (61 g, 620 mmol) and the reaction mixture was stirred at 100° C. under argon for 16 h.

Further 4,4,4',4',5,5,5',5'-octamethyl-2,2'-bi(1,3,2-dioxaborolane) (131.2 g, 516.4 mmol), [1,1'-bis(diphenylphosphino)ferrocene] dichloro palladium(II) (6.4 g, 8.6 mmol) and potassium acetate (34 g, 344.24 mmol) were added, the reaction mixture was stirred at 100° C. under argon for 16 h. The solvent was removed and the residue purified by column chromatography (silica, 200-300 mesh, 2000 g, petroleum ether/ethyl acetate 30:1 to DCM/MeOH=200:1) to give methyl 3-(6-chloro-3-oxo-7-(4,4,5,5-tetramethyl-1,3,2-dioxaborolan-2-yl)-2H-benzo[b][1,4]oxazin-4(3H)-yl)propanoate as a yellow solid (86 g, crude).

LCMS: Rt 1.75 min, MH$^+$ 396.

Intermediate 7: Methyl 3-(6-chloro-7-hydroxy-3-oxo-2H-benzo[b][1,4]oxazin-4(3H)-yl)propanoate

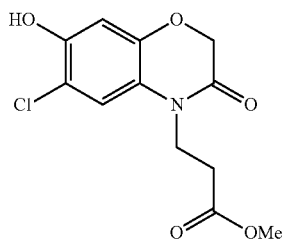 [SMILES: COC(=O)CCN1C(=O)COc2cc(O)c(Cl)cc21]

To methyl 3-(6-chloro-3-oxo-7-(4,4,5,5-tetramethyl-1,3,2-dioxaborolan-2-yl)-2H-benzo[b][1,4]oxazin-4(3H)-yl)propanoate (86 g, 217.4 mmol) in THF (1000 mL), was added acetic acid (150 mL), hydrogen peroxide (30%, 150 mL) and the reaction mixture stirred at room temperature for 2 h. The mixture was poured into water (1000 mL), extracted with dichloromethane (500 mL×3) and the combined organics dried over sodium sulphate. The residue was purified by column chromatography (silica, 200-300 mesh, 600 g, petroleum ether/ethyl acetate 5:1 to DCM/MeOH 200:1). The resulting yellow solid (25.5 g) was recrystallised from ethyl acetate (200 mL) to afford methyl 3-(6-chloro-7-hydroxy-3-oxo-2H-benzo[b][1,4]oxazin-4(3H)-yl)propanoate as a yellow solid (13.89 g).

LCMS: Rt 1.41 min, MH$^+$ 286.

Intermediate 8: 1-(5-chloropyridin-2-yl)propan-1-one

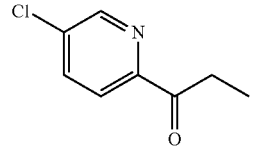

To a solution of 5-chloropicolinonitrile (12.5 g, 90.2 mmol) dissolved in THF (200 mL) at 0° C. ethylmagnesium bromide (3 M in THF, 54 mL, 162 mmol) was added drop wise. After addition, the mixture was stirred at 0° C. for 2 h. After the completion of the reaction, water (500 mL) was added drop wise at 0° C., the mixture extracted with ethyl acetate (100 mL×3) and the combined organic phases dried over sodium sulphate. The mixture was filtered and the solvent removed. The residue was purified by column chromatography (silica:200-300 mesh, 40 g, petroleum ether/ethyl acetate 10:1, 800 mL) to give 1-(5-chloropyridin-2-yl)propan-1-one as a yellow oil (10 g).

LCMS: Rt 1.59 min, MH$^+$ 170/172.

Intermediate 9: 1-(5-chloropyridin-2-yl)propan-1-ol

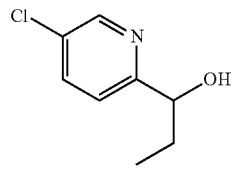

To a solution of 1-(5-chloropyridin-2-yl)propan-1-one (9.5 g, 56 mmol) in methanol (100 mL), sodium borohydride (2.12 g, 56 mmol) was added slowly at room temperature. Water (500 mL) was added, the mixture extracted with ethyl acetate (100 mL×4) and the combined organic phases dried over sodium sulphate. The solvent was removed to give 1-(5-chloropyridin-2-yl)propan-1-ol as a yellow oil (9.6 g).

Intermediate 10: 1-(5-chloropyridin-2-yl)propyl methanesulfonate

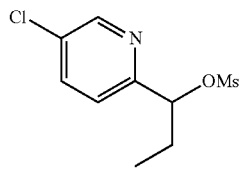

1-(5-Chloropyridin-2-yl)propan-1-ol (9.6 g, 56.1 mmol), triethyl amine (6.8 g, 67.4 mmol) was mixed in DCM (150 mL) at 0° C. Methanesulfonyl chloride (6.43 g, 56.1 mmol) was added dropwise and, after addition, the mixture was stirred at room temperature for 2 h. The solvent was removed and the residue was purified by column chromatography (silica:200-300 mesh, 40 g, petroleum ether/ethyl acetate 4:1, 1500 mL) to give 1-(5-chloropyridin-2-yl)propyl methanesulfonate as a yellow oil (13.97 g).

Intermediates 11 and 12: (R)-methyl 3-(6-chloro-7-(1-(5-chloropyridin-2-yl)propoxy)-3-oxo-2H-benzo[b][1,4]oxazin-4(3H)-yl)propanoate (Intermediate 11) and (S)-methyl 3-(6-chloro-7-(1-(5-chloropyridin-2-yl)propoxy)-3-oxo-2H-benzo[b][1,4]oxazin-4(3H)-yl)propanoate (Intermediate 12)

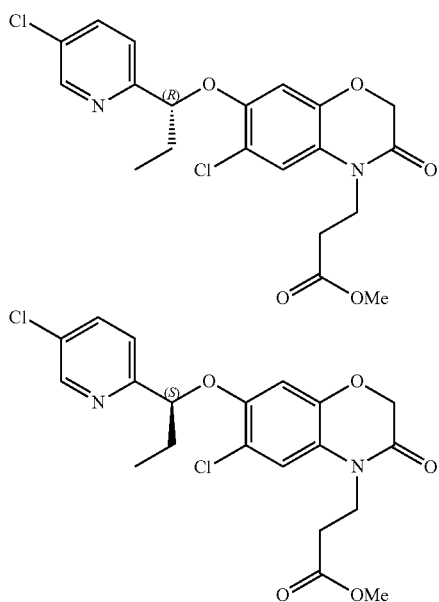

1-(5-Chloropyridin-2-yl)propyl methanesulfonate (13.97 g, 56.1 mmol), methyl 3-(6-chloro-7-hydroxy-3-oxo-2H-benzo[b][1,4]oxazin-4(3H)-yl)propanoate (16 g, 56.1 mmol), potassium carbonate (9.3 g, 67.3 mmol) and MeCN (250 mL) were mixed and stirred at 80° C. for 16 h. The solvent was removed and the residue was purified by column chromatography (silica:200-300 mesh, 80 g, petroleum ether/ethyl acetate 4:1, 2500 mL) to give methyl 3-(6-chloro-7-(1-(5-chloropyridin-2-yl)propoxy)-3-oxo-2H-benzo[b][1,4]oxazin-4(3H)-yl)propanoate as a yellow oil (23 g).

The enantiomers were separated by chiral-prep-HPLC [chiralpak-AD-H, 250×20 mm, 5 µm, eluent: carbon dioxide, IPA (formic acid+DEA)] to give (R)-methyl 3-(6-chloro-7-(1-(5-chloropyridin-2-yl)propoxy)-3-oxo-2H-benzo[b][1,4]oxazin-4(3H)-yl)propanoate as a yellow oil (9.0 g) and (S)-methyl 3-(6-chloro-7-(1-(5-chloropyridin-2-yl)propoxy)-3-oxo-2H-benzo[b][1,4]oxazin-4(3H)-yl)propanoate as a yellow oil (8.4 g).

(R)-methyl 3-(6-chloro-7-(1-(5-chloropyridin-2-yl)propoxy)-3-oxo-2H-benzo[b][1,4]oxazin-4(3H)-yl)propanoate (Intermediate 11). Chiral HPLC: Rt=3.33 min.

(S)-methyl 3-(6-chloro-7-(1-(5-chloropyridin-2-yl)propoxy)-3-oxo-2H-benzo[b][1,4]oxazin-4(3H)-yl)propanoate (Intermediate 12). Chiral HPLC: Rt=5.55 min

Intermediate 13: (S)-1-(5-chloropyridin-2-yl)propan-1-ol

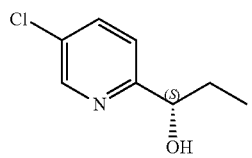

(R)-3,3-Diphenyl-1-methylpyrrolidino[1,2-c]-1,3,2-oxazaborole (1N in toluene, 10.61 mL, 10.61 mmol) in THF (50 mL) was cooled to 0° C., borane-methyl sulfide complex (2 N in THF, 5.3 mL, 10.6 mmol) was added and the mixture was stirred at 0° C. for 1 h. 1-(5-Chloropyridin-2-yl)propan-1-one (1.8 g, 10.61 mol) in THF (5 mL) was added at 0° C., and the reaction mixture was warmed to room temperature and stirred for 16 h. Methanol (2 mL) was added and the mixture was stirred at room temperature for 15 min. The solvent was removed and the residue was purified by column chromatography (silica, 200-300 mesh, 30 g, petroleum ether/ethyl acetate 5:1) to give (S)-1-(5-chloropyridin-2-yl)propan-1-ol as a colourless oil (0.52 g).

LCMS: Rt 1.33 min, MH$^+$ 172.

Intermediate 14: (R)-methyl 3-(6-chloro-7-(1-(5-chloropyridin-2-yl)propoxy)-3-oxo-2H-benzo[b][1,4] oxazin-4(3H)-yl)propanoate

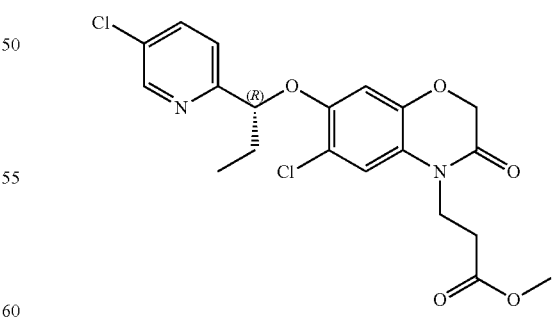

To methyl 3-(6-chloro-7-hydroxy-3-oxo-2H-benzo[b][1,4]oxazin-4(3H)-yl)propanoate (Intermediate 7; 1.3 g) in THF (100 mL) at 0° C. were added (S)-1-(5-chloropyridin-2-yl)propan-1-ol (520 mg, 3.03 mmol), triphenylphosphine (1.6 g, 6.06 mmol) and diethyl azodicarboxylate (1.1 g, 6.06 mmol). After addition, the reaction mixture was warmed to room temperature and stirred for 16 h. The solvent was removed and the residue purified by column chromatography [silica, 200-300 mesh, 50 g, petroleum ether/ethyl acetate 4:1] to give (R)-methyl 3-(6-chloro-7-(1-(5-chloropyridin-2-yl)propoxy)-3-oxo-2H-benzo[b][1,4] oxazin-4 (3H)-yl)propanoate as a yellow oil (10.8 g).

LCMS: Rt 1.70 min, MH+ 439/441.

Example 1

(R)-3-(6-Chloro-7-(1-(5-chloropyridin-2-yl) propoxy)-3-oxo-2H-benzo[b][1,4]oxazin-4(3H)-yl) propanoic Acid

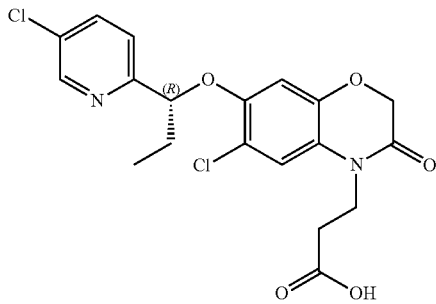

(R)-Methyl 3-(6-chloro-7-(1-(5-chloropyridin-2-yl)propoxy)-3-oxo-2H-benzo[b][1,4]oxazin-4(3H)-yl)propanoate (9.0 g, 20.5 mmol), THF (50 mL) and lithium hydroxide (0.5 N in water, 50 mL) were mixed and the reaction was stirred at room temperature for 2 h. Water (150 mL) was added and the mixture extracted with ethyl acetate (50 mL×3). The separated aqueous phase was adjusted to pH 6-7 with hydrochloric acid (0.5 N). The mixture was filtered and the solid was collected and dried over air to give (R)-3-(6-chloro-7-(1-(5-chloropyridin-2-yl)propoxy)-3-oxo-2H-benzo[b][1,4]oxazin-4(3H)-yl)propanoic acid as a white solid (6.5 g).

LCMS: Rt 1.59 min, MH+ 425/427;

$^1$H NMR (300 MHz, d$_6$-DMSO) δ 12.37 (s, 1H), 8.63 (d, J=2.4 Hz, 1H), 7.95 (dd, J=8.4, 2.5 Hz, 1H), 7.46 (d, J=8.4 Hz, 1H), 7.38 (s, 1H), 6.66 (s, 2H), 5.36 (t, J=6.2 Hz, 1H), 4.04 (t, J=7.4 Hz, 2H), 2.10-1.88 (m, 3H), 0.92 (t, J=7.3 Hz, 3H).

Example 1 (Alternative Preparation)

(R)-3-(6-Chloro-7-(1-(5-chloropyridin-2-yl) propoxy)-3-oxo-2H-benzo[b][1,4]oxazin-4(3H)-yl) propanoic Acid

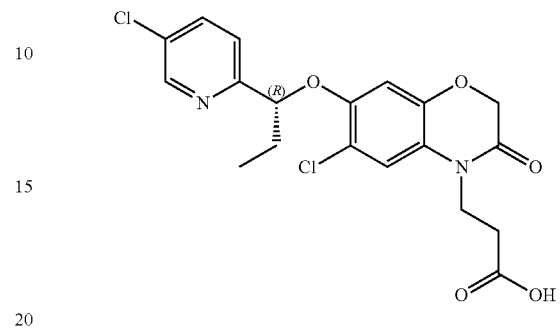

To (R)-methyl 3-(6-chloro-7-(1-(5-chloropyridin-2-yl)propoxy)-3-oxo-2H-benzo[b][1,4]oxazin-4(3H)-yl)propanoate (0.8 g, 2.05 mmol) in THF (50 mL) was added lithium hydroxide (1N, 8.2 mL, 8.2 mmol) and the mixture stirred at room temperature for 2 h. The solvent was removed, hydrochloric acid (0.5 N) added to adjust the mixture to pH 5 and the mixture extracted with ethyl acetate (20 mL×5). The combined organic extracts were dried over sodium sulphate, the solvent removed and the residue purified with prep-HPLC (column: Diasogel C18 250×50 mm, 10 um; eluent: ACN-H$_2$O=50-80, 0.1% formic acid) to give (R)-3-(6-chloro-7-(1-(5-chloropyridin-2-yl)propoxy)-3-2H-benzo[b][1,4]oxazin-4(3H)-yl)propanoic acid as a white solid (590 mg).

LCMS: Rt 1.60 min, MH+ 425/427;

$^1$H NMR (300 MHz, CD$_3$OD) δ 8.54 (d, J=2.4 Hz, 1H), 7.83 (dd, J=8.4, 2.5 Hz, 1H), 7.46 (d, J=8.5 Hz, 1H), 7.27 (s, 1H), 6.52 (s, 1H), 5.27-5.16 (m, 1H), 4.51 (d, J=1.5 Hz, 2H), 4.20-4.09 (m, 2H), 2.66-2.54 (m, 2H), 2.04 (dd, J=13.0, 5.9 Hz, 2H), 1.03 (t, J=7.4 Hz, 3H).

Examples 2-30 were prepared substantially according to Reaction Scheme 1 using methyl 3-(6-chloro-7-hydroxy-3-oxo-2H-benzo[b][1,4]oxazin-4(3H)-yl)propanoate and the appropriate alcohol or mesylate, which may be commercially available or prepared substantially according to Reaction Schemes 2, 3, 4 or 5.

| Example no. | Name | Structure | Molecular ion + Identity | Retention Time (min) |
|---|---|---|---|---|
| 2 | 2-amino-2-(hydroxymethyl)propane-1,3-diol; 3-{6-chloro-3-oxo-7-[(1R)-1-(pyridin-2-yl)ethoxy]-3,4-dihydro-2H-1,4-benzoxazin-4-yl}propanoic acid | 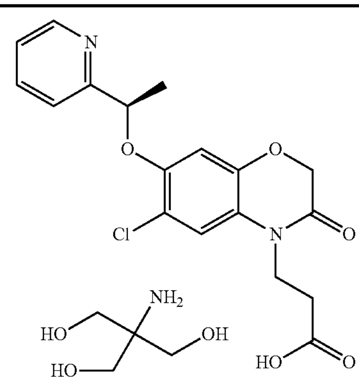 | 377 (MH+) | 1.37 |

-continued

| Example no. | Name | Structure | Molecular ion + Identity | Retention Time (min) |
|---|---|---|---|---|
| 2a | 3-{6-chloro-3-oxo-7-[(1R)-1-(pyridin-2-yl)ethoxy]-3,4-dihydro-2H-1,4-benzoxazin-4-yl}propanoic acid | 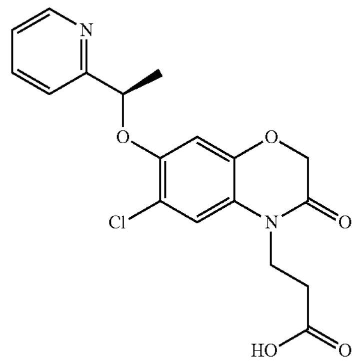 [SMILES: C[C@@H](Oc1cc2c(cc1Cl)N(CCC(=O)O)C(=O)CO2)c1ccccn1] | 377 (MH+) | 1.35 |
| 2b | 3-{6-chloro-3-oxo-7-[(1R)-1-(pyridin-2-yl)ethoxy]-3,4-dihydro-2H-1,4-benzoxazin-4-yl}propanoic acid hydrochloride | 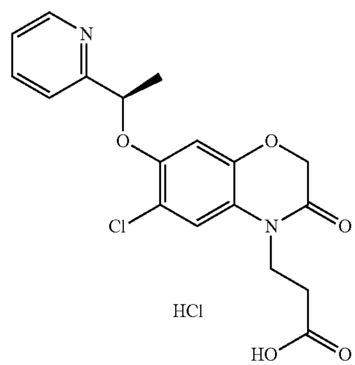 [SMILES: C[C@@H](Oc1cc2c(cc1Cl)N(CCC(=O)O)C(=O)CO2)c1ccccn1 ; Cl] | 377 (MH+) | 1.36 |
| 2c | (2S)-2-amino-5-carbamimidamido pentanoic acid; 3-{6-chloro-3-oxo-7-[(1R)-1-(pyridin-2-yl)ethoxy]-3,4-dihydro-2H-1,4-benzoxazin-4-yl}propanoic acid | | 377 (MH+) | 1.36 |

-continued

| Example no. | Name | Structure | Molecular ion + Identity | Retention Time (min) |
|---|---|---|---|---|
| 2d | (2S)-2,6-diaminohexanoic acid; 3-{6-chloro-3-oxo-7-[(1R)-1-(pyridin-2-yl)ethoxy]-3,4-dihydro-2H-1,4-benzoxazin-4-yl}propanoic acid | 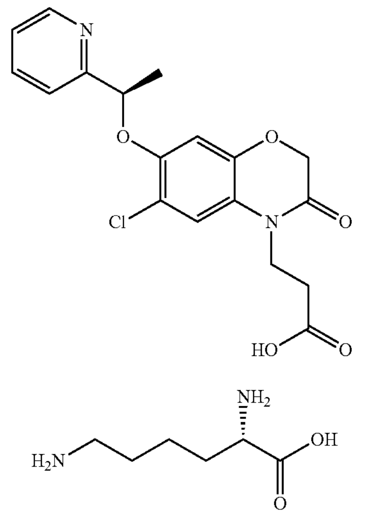 | 377 (MH+) | 1.36 |
| 2e | 3-{6-chloro-3-oxo-7-[(1R)-1-(pyridin-2-yl)ethoxy]-3,4-dihydro-2H-1,4-benzoxazin-4-yl}propanoic acid; benzyl[2-(benzylamino)ethyl]amine | 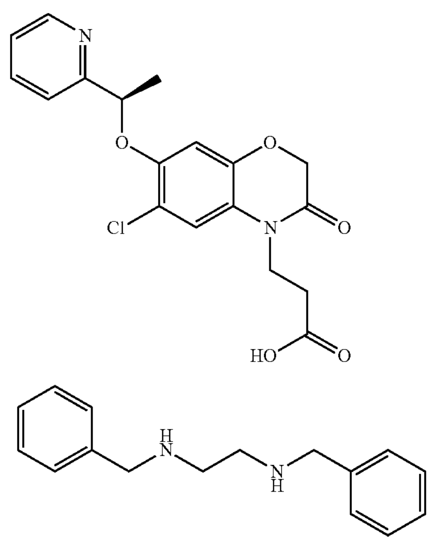 [SMILES: C[C@@H](Oc1cc2c(cc1Cl)N(CCC(=O)O)C(=O)CO2)c1ccccn1 ; c1ccc(CNCCNCc2ccccc2)cc1] | 377 (MH+) | 1.36 |
| 2f | 3-{6-chloro-3-oxo-7-[(1R)-1-(pyridin-2-yl)ethoxy]-3,4-dihydro-2H-1,4-benzoxazin-4-yl}propanoic acid; sulfuric acid | 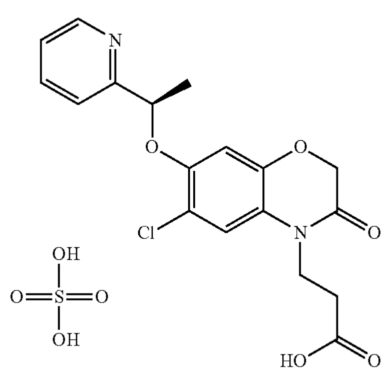 [SMILES: O=S(=O)(O)O ; C[C@@H](Oc1cc2c(cc1Cl)N(CCC(=O)O)C(=O)CO2)c1ccccn1] | 377 (MH+) | 1.45 |

| Example no. | Name | Structure | Molecular ion + Identity | Retention Time (min) |
|---|---|---|---|---|
| 2g | 3-{6-chloro-3-oxo-7-[(1R)-1-(pyridin-2-yl)ethoxy]-3,4-dihydro-2H-1,4-benzoxazin-4-yl}propanoic acid; methanesulfonic acid | 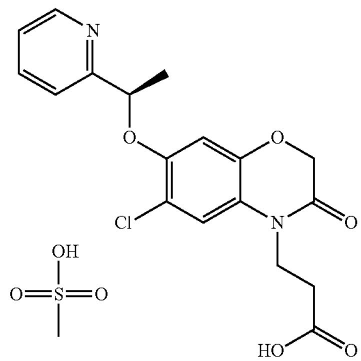 | 377 (MH+) | 1.46 |
| 2h | 3-{6-chloro-3-oxo-7-[(1R)-1-(pyridin-2-yl)ethoxy]-3,4-dihydro-2H-1,4-benzoxazin-4-yl}propanoic acid; 4-methylbenzene-1-sulfonic acid | 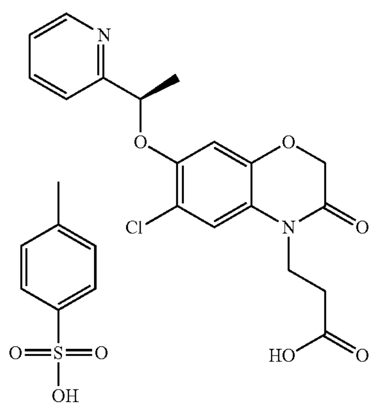 | 377 (MH+) | 1.28 |
| 2i | 3-{6-chloro-3-oxo-7-[(1R)-1-(pyridin-2-yl)ethoxy]-3,4-dihydro-2H-1,4-benzoxazin-4-yl}propanoic acid; benzyl(2-phenylethyl)amine | 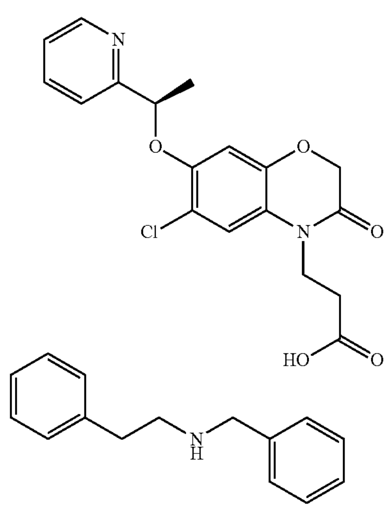 | 377 (MH+) | 1.36 |

| Example no. | Name | Structure | Molecular ion + Identity | Retention Time (min) |
|---|---|---|---|---|
| 2j | 3-{6-chloro-3-oxo-7-[(1R)-1-(pyridin-2-yl)ethoxy]-3,4-dihydro-2H-1,4-benzoxazin-4-yl}propanoic acid; bis(2-aminoethyl)amine | 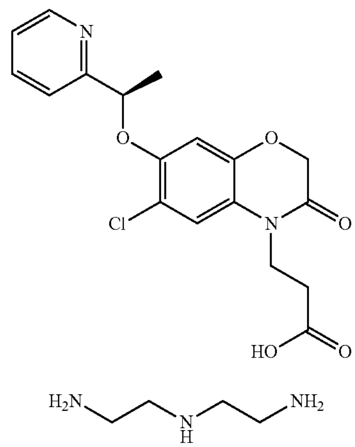 | 377 (MH+) | 1.37 |
| 2k | (2R,3R,4R,5S)-6-(methylamino)hexane-1,2,3,4,5-pentol; 3-{6-chloro-3-oxo-7-[(1R)-1-(pyridin-2-yl)ethoxy]-3,4-dihydro-2H-1,4-benzoxazin-4-yl}propanoic acid | 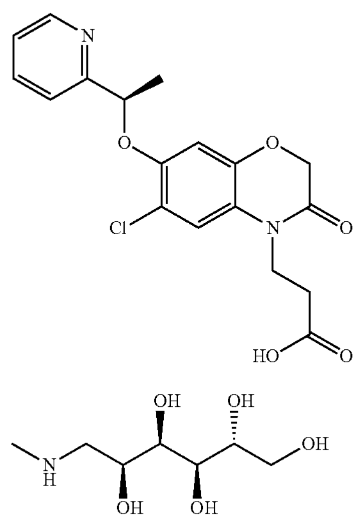 | 377 (MH+) | 1.36 |
| 2l | sodium 3-{6-chloro-3-oxo-7-[(1R)-1-(pyridin-2-yl)ethoxy]-3,4-dihydro-2H-1,4-benzoxazin-4-yl}propanoate | 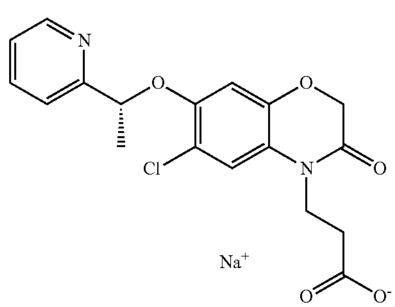 [SMILES: C[C@@H](Oc1cc2c(cc1Cl)N(CCC(=O)[O-])C(=O)CO2)c1ccccn1 ; [Na+]] | 377 (MH+) | 1.36 |

-continued

| Example no. | Name | Structure | Molecular ion + Identity | Retention Time (min) |
|---|---|---|---|---|
| 3 | 2-amino-2-(hydroxymethyl)propane-1,3-diol; 3-{6-chloro-7-[1-(2-methyl-1,3-oxazol-5-yl)ethoxy]-3-oxo-3,4-dihydro-2H-1,4-benzoxazin-4-yl}propanoic acid racemate | 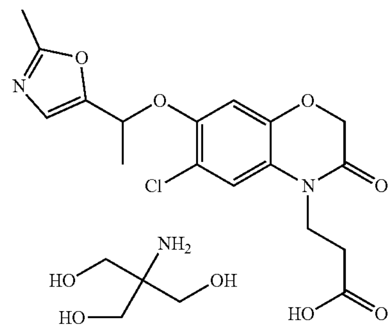 | 381/383 (MH+) | 1.35 |
| 4 | 2-amino-2-(hydroxymethyl)propane-1,3-diol; 3-{6-chloro-7-[1-(1,3-oxazol-2-yl)ethoxy]-3-oxo-3,4-dihydro-2H-1,4-benzoxazin-4-yl}propanoic acid single unidentified enantiomer | ISOMER 1 | 367/369 (MH+) | 1.43 |
| 5 | 2-amino-2-(hydroxymethyl)propane-1,3-diol; 3-{6-chloro-7-[1-(1,3-oxazol-2-yl)ethoxy]-3-oxo-3,4-dihydro-2H-1,4-benzoxazin-4-yl}propanoic acid single unidentified enantiomer | ISOMER 2 | 367/369 (MH+) | 1.43 |

-continued

| Example no. | Name | Structure | Molecular ion + Identity | Retention Time (min) |
|---|---|---|---|---|
| 6 | 2-amino-2-(hydroxymethyl)propane-1,3-diol; 3-{6-chloro-7-[1-(1H-imidazol-2-yl)ethoxy]-3-oxo-3,4-dihydro-2H-1,4-benzoxazin-4-yl}propanoic acid racemate | 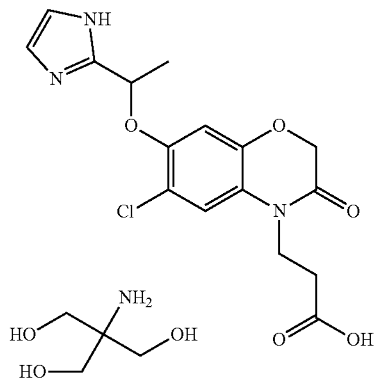 [SMILES: CC(Oc1cc2c(cc1Cl)N(CCC(=O)O)C(=O)CO2)c1ncc[nH]1 ; NC(CO)(CO)CO] | 366 (MH+) | 1.18 |
| 7 | 2-amino-2-(hydroxymethyl)propane-1,3-diol; 3-{6-chloro-3-oxo-7-[1-(pyrimidin-2-yl)ethoxy]-3,4-dihydro-2H-1,4-benzoxazin-4-yl}propanoic acid single unidentified enantiomer | ISOMER 1 | 378 (MH+) | 1.32 |
| 8 | 2-amino-2-(hydroxymethyl)propane-1,3-diol; 3-{6-chloro-3-oxo-7-[1-(pyrimidin-2-yl)ethoxy]-3,4-dihydro-2H-1,4-benzoxazin-4-yl}propanoic acid single unidentified enantiomer | ISOMER 2 | 378 (MH+) | 1.32 |
| 9 | 3-[6-chloro-3-oxo-7-(pyridin-2-ylmethoxy)-3,4-dihydro-2H-1,4-benzoxazin-4-yl]propanoic acid | 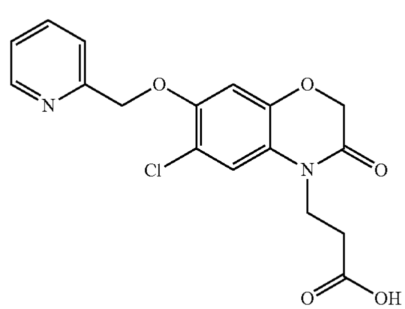 [SMILES: O=C(O)CCN1C(=O)COc2cc(OCc3ccccn3)c(Cl)cc21] | 363/365 (MH+) | 1.31 |

-continued

| Example no. | Name | Structure | Molecular ion + Identity | Retention Time (min) |
|---|---|---|---|---|
| 10 | 3-{6-chloro-7-[(1R)-1-(5-methylpyridin-2-yl)ethoxy]-3-oxo-3,4-dihydro-2H-1,4-benzoxazin-4-yl}propanoic acid | 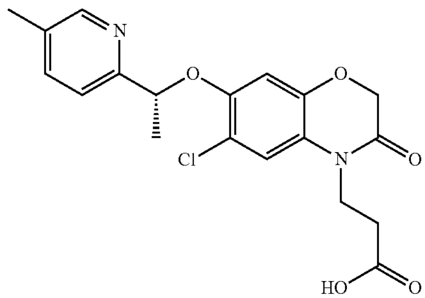 [SMILES: Cc1ccc([C@@H](C)Oc2cc3c(cc2Cl)N(CCC(=O)O)C(=O)CO3)nc1] | 391 (MH+) | 1.40 |
| 11 | 3-{6-chloro-7-[(1R)-1-(5-chloropyridin-2-yl)ethoxy]-3-oxo-3,4-dihydro-2H-1,4-benzoxazin-4-yl}propanoic acid | 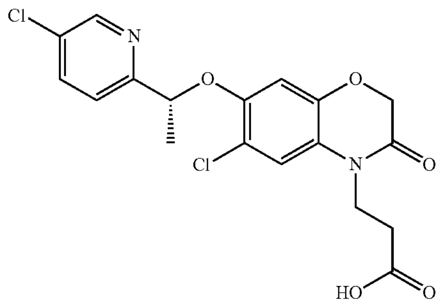 [SMILES: C[C@@H](Oc1cc2c(cc1Cl)N(CCC(=O)O)C(=O)CO2)c1ccc(Cl)cn1] | 411 (MH+) | 1.58 |
| 12 | 3-{6-chloro-7-[(1R)-1-(5-fluoropyridin-2-yl)ethoxy]-3-oxo-3,4-dihydro-2H-1,4-benzoxazin-4-yl}propanoic acid | 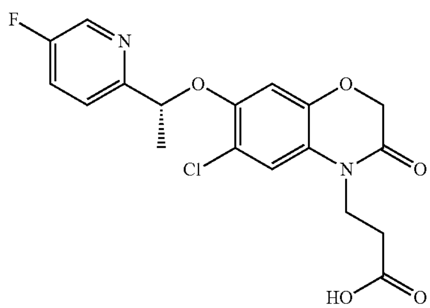 [SMILES: C[C@@H](Oc1cc2c(cc1Cl)N(CCC(=O)O)C(=O)CO2)c1ccc(F)cn1] | 395 (MH+) | 1.45 |
| 13 | 3-{6-chloro-3-oxo-7-[(1R)-1-(pyridazin-3-yl)ethoxy]-3,4-dihydro-2H-1,4-benzoxazin-4-yl}propanoic acid | 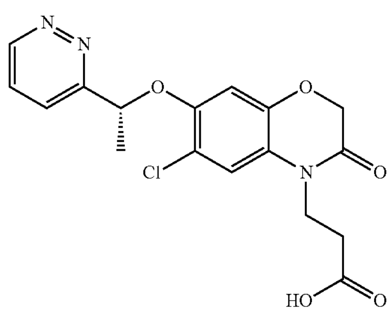 [SMILES: C[C@@H](Oc1cc2c(cc1Cl)N(CCC(=O)O)C(=O)CO2)c1cccnn1] | 378/380 (MH+) | 1.28 |
| 14 | 3-{6-chloro-7-[(6-methylpyridazin-3-yl)methoxy]-3-oxo-3,4-dihydro-2H-1,4-benzoxazin-4-yl}propanoic acid | 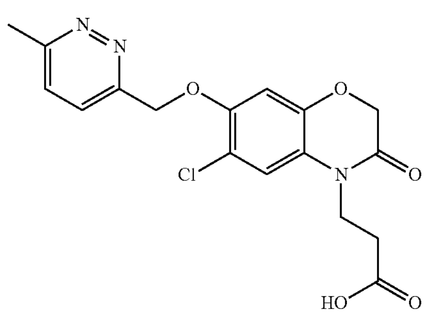 [SMILES: Cc1ccc(COc2cc3c(cc2Cl)N(CCC(=O)O)C(=O)CO3)nn1] | 378 (MH+) | 1.49 |

-continued

| Example no. | Name | Structure | Molecular ion + Identity | Retention Time (min) |
|---|---|---|---|---|
| 15 | 3-{6-chloro-7-[(1R)-1-(6-methylpyridazin-3-yl)ethoxy]-3-oxo-3,4-dihydro-2H-1,4-benzoxazin-4-yl}propanoic acid | 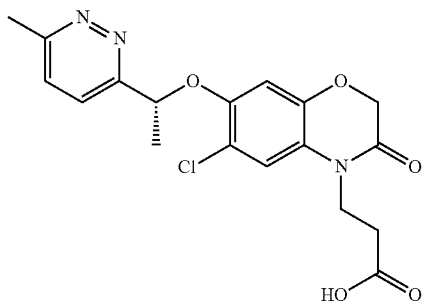 [SMILES: Cc1ccc([C@@H](C)Oc2cc3c(cc2Cl)N(CCC(=O)O)C(=O)CO3)nn1] | 392 (MH+) | 1.29 |
| 16 | 3-{6-chloro-7-[(1R)-1-(5-methylpyridin-2-yl)propoxy]-3-oxo-3,4-dihydro-2H-1,4-benzoxazin-4-yl}propanoic acid | 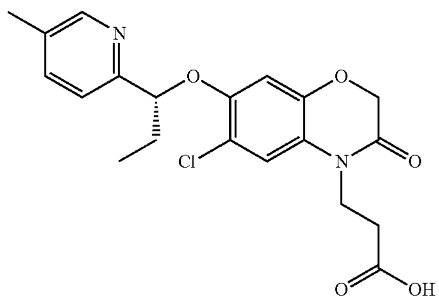 [SMILES: CC[C@@H](Oc1cc2c(cc1Cl)N(CCC(=O)O)C(=O)CO2)c1ccc(C)cn1] | 405 (MH+) | 1.48 |
| 17 | 3-{6-chloro-3-oxo-7-[(1R)-1-(pyridin-2-yl)propoxy]-3,4-dihydro-2H-1,4-benzoxazin-4-yl}propanoic acid | 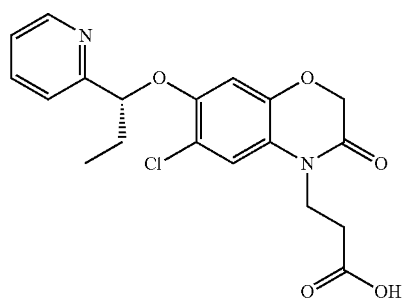 [SMILES: CC[C@@H](Oc1cc2c(cc1Cl)N(CCC(=O)O)C(=O)CO2)c1ccccn1] | 391 (MH+) | 1.44 |
| 18 | 3-{6-chloro-7-[(5-chloropyridin-2-yl)methoxy]-3-oxo-3,4-dihydro-2H-1,4-benzoxazin-4-yl}propanoic acid | 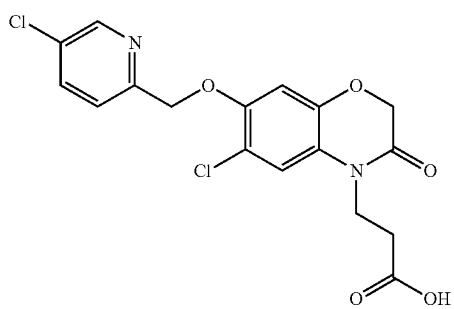 [SMILES: O=C(O)CCN1C(=O)COc2cc(OCc3ccc(Cl)cn3)c(Cl)cc21] | 397/399 (MH+) | 1.49 |
| 19 | 3-{6-chloro-7-[(5-methylpyridin-2-yl)methoxy]-3-oxo-3,4-dihydro-2H-1,4-benzoxazin-4-yl}propanoic acid | 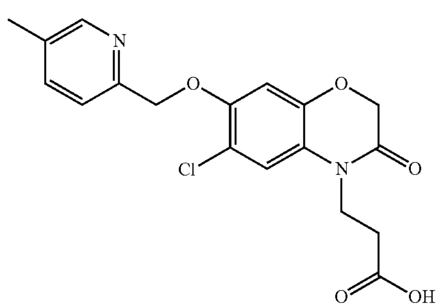 [SMILES: Cc1ccc(COc2cc3c(cc2Cl)N(CCC(=O)O)C(=O)CO3)nc1] | 377/379 (MH+) | 1.35 |

-continued

| Example no. | Name | Structure | Molecular ion + Identity | Retention Time (min) |
|---|---|---|---|---|
| 20 | 3-{6-chloro-7-[(1R)-1-(5-ethylpyridin-2-yl)ethoxy]-3-oxo-3,4-dihydro-2H-1,4-benzoxazin-4-yl}propanoic acid | 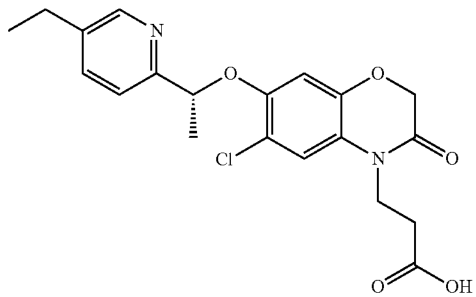 [SMILES: CCc1ccc([C@@H](C)Oc2cc3c(cc2Cl)N(CCC(=O)O)C(=O)CO3)nc1] | 405 (MH+) | 1.48 |
| 21 | 3-{6-chloro-3-oxo-7-[1-(pyrimidin-2-yl)propoxy]-3,4-dihydro-2H-1,4-benzoxazin-4-yl}propanoic acid single unidentified enantiomer | ISOMER 1 | 392/394 (MH+) | 1.37 |
| 22 | 3-{6-chloro-3-oxo-7-[1-(pyrimidin-2-yl)propoxy]-3,4-dihydro-2H-1,4-benzoxazin-4-yl}propanoic acid single unidentified enantiomer | ISOMER 2 | 392/394 (MH+) | 1.37 |
| 23 | 3-{6-chloro-7-[1-(5-methylpyrimidin-2-yl)propoxy]-3-oxo-3,4-dihydro-2H-1,4-benzoxazin-4-yl}propanoic acid single unidentified enantiomer | ISOMER 1 | 406/408 (MH+) | 1.44 |

| Example no. | Name | Structure | Molecular ion + Identity | Retention Time (min) |
|---|---|---|---|---|
| 24 | 3-{6-chloro-7-[1-(5-methylpyrimidin-2-yl)propoxy]-3-oxo-3,4-dihydro-2H-1,4-benzoxazin-4-yl}propanoic acid single unidentified enantiomer | ISOMER 2 | 406/408 (MH+) | 1.44 |
| 25 | 3-{6-chloro-7-[1-(5-chloropyrimidin-2-yl)propoxy]-3-oxo-3,4-dihydro-2H-1,4-benzoxazin-4-yl}propanoic acid single unidentified enantiomer | ISOMER 1 | 426/428 (MH+) | 1.50 |
| 26 | 3-{6-chloro-7-[1-(5-chloropyrimidin-2-yl)propoxy]-3-oxo-3,4-dihydro-2H-1,4-benzoxazin-4-yl}propanoic acid single unidentified enantiomer | ISOMER 2 | 426/428 (MH+) | 1.53 |
| 27 | 3-{6-chloro-3-oxo-7-[1-(pyridazin-3-yl)propoxy]-3,4-dihydro-2H-1,4-benzoxazin-4-yl}propanoic acid single unidentified enantiomer | ISOMER 1 | 392 (MH+) | 1.33 |

| Example no. | Name | Structure | Molecular ion + Identity | Retention Time (min) |
|---|---|---|---|---|
| 28 | 3-{6-chloro-3-oxo-7-[1-(pyridazin-3-yl)propoxy]-3,4-dihydro-2H-1,4-benzoxazin-4-yl}propanoic acid single unidentified enantiomer | 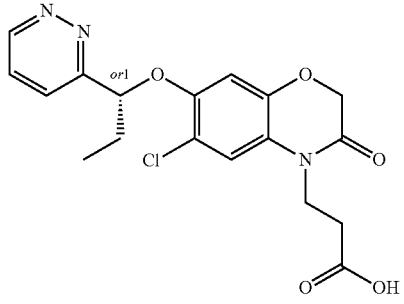 ISOMER 2 | 392 (MH+) | 1.33 |
| 29 | 3-{6-chloro-7-[1-(6-methylpyridazin-3-yl)propoxy]-3-oxo-3,4-dihydro-2H-1,4-benzoxazin-4-yl}propanoic acid single unidentified enantiomer | 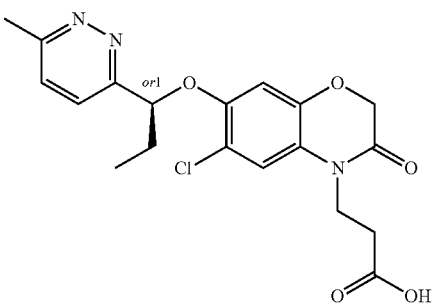 ISOMER 1 | 406 (MH+) | 1.37 |
| 30 | 3-{6-chloro-7-[1-(6-methylpyridazin-3-yl)propoxy]-3-oxo-3,4-dihydro-2H-1,4-benzoxazin-4-yl}propanoic acid single unidentified enantiomer | 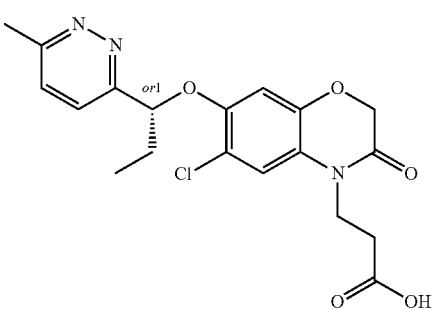 ISOMER 2 | 406 (MH+) | 1.37 |

Methods of Use

In general, the present invention relates to methods or uses for treating pancreatitis, kidney diseases and other various disorders as described herein, for conditions or disorders mediated by KMO inhibitors, which comprises administering 6-chlorobenzoxazine compounds of Formula (I) or pharmaceutically acceptable salts or pharmaceutical compositions thereof.

Certain compounds of the invention are inhibitors of KMO. Compounds which inhibit KMO may be useful in the treatment of various conditions or disorders mediated by KMO, for example acute pancreatitis, chronic kidney disease, acute kidney disease, acute kidney injury, other conditions associated with systemic inflammatory response syndrome (SIRS), Huntington's disease, Alzheimer's disease, spinocerebellar ataxias, Parkinson's disease, AIDS-dementia complex, HIV infection, amylotrophic lateral sclerosis (ALS), depression, schizophrenia, sepsis, cardiovascular shock, severe trauma, acute lung injury, acute respiratory distress syndrome, acute cholecystitis, severe burns, pneumonia, extensive surgical procedures, ischemic bowel disease, severe acute hepatic disease, severe acute hepatic encephalopathy or acute renal failure.

Additional conditions or disorders include hyperproliferative diseases of benign or malignant behaviour, in which cells of various tissues and organs exhibit aberrant patterns of growth, proliferation, migration, signalling, senescence, and death. Generally hyperproliferative disease refers to diseases and disorders associated with the uncontrolled proliferation of cells, including but not limited to uncontrolled growth of organ and tissue cells resulting in cancers and benign tumours. Hyperproliferative disorders associated with endothelial cells can result in diseases of angiogenesis such as angiomas, endometriosis, obesity, age-related macular degeneration and various retinopathies, as well as the proliferation of ECs and smooth muscle cells that cause restenosis as a consequence of stenting in the treatment of atherosclerosis. Hyperproliferative disorders involving fibroblasts (i.e. fibrogenesis) include but are not limited to disorders of excessive scaring (i.e. fibrosis) such as age-related macular degeneration, cardiac remodelling and failure associated with myocardial infarction, excessive wound healing such as commonly occurs as a consequence of surgery or injury, keloids, and fibroid tumours and stenting.

Further such conditions or disorders include transplant rejection (suppression of T-cells) and graft vs host disease, systemic inflammatory disorders, brain inflammatory disorders including malaria and African trypanosomiasis, and pneumococcal meningitis.

Further such conditions or disorders include cirrhosis, chronic pancreatitis, liver fibrosis, lung fibrosis and ischemia-reperfusion injury Further such conditions or disorders include, for example, neurodegenerative diseases, psychiatric or neurological diseases or disorders, Creutzfeld-Jacob disease, trauma-induced neurodegeneration, high-pressure neurological syndrome, dystonia, olivopontocerebellar atrophy, multiple sclerosis, epilepsy, consequences of stroke, cerebral ischemia, ischemic disorders including stroke (focal ischemia), hypoxia, multi-infarct dementia, consequences of cerebral trauma or damage, damage to the spinal cord, dementia such as senile dementia, AIDS-induced encephalopathy, other infection related encephalopathy, viral or bacterial meningitis, infectious diseases caused by viral, bacterial and other parasites, (for example, general central nervous system (CNS) infections such as viral, bacterial or parasitic infection, for example, poliomyelitis, Lyme disease (*Borrelia burgdorferi* infection)) septic shock, and cancers, cancers with cerebral localization, hepatic encephalopathy, systemic lupus, analgesia and opiate withdrawal symptoms, feeding behaviour, psychiatric disorders, such as insomnia, severe deficit in working memory, severe deficit in long term memory storage, decrease in cognition, severe deficit in attention, severe deficit in executive functioning, slowness in information processing, slowness in neural activity, anxiety, generalized anxiety disorders, panic anxiety, obsessive compulsive disorders, social phobia, performance anxiety, post-traumatic stress disorder, acute stress reaction, adjustment reaction, separation anxiety disorder, alcohol withdrawal anxiety, depressive disorders, disorders of the developing or aged brain, diabetes, and complications thereof, Tourette's syndrome, Fragile X syndrome, autism spectrum disorders, disorders that cause severe and pervasive impairment in thinking feeling, language and the ability to relate to others, mood disorders, psychological disorders characterized by abnormalities of emotional state, such as without limitation, bipolar disorder, unipolar depression, major depression, endogenous depression, involutional depression, reactive depression, psychotic depression, depression caused by underlying medical conditions, cyclothymic disorders, dysthymic disorders, mood disorders due to general medical condition, mood disorders not otherwise specified and substance-induced mood disorders.

Further such conditions or disorders also include, for example, acute necrotizing pancreatitis, AIDS (disease), aseptic meningitis, brain disease, for example, Gilles de la Tourette syndrome, Asperger syndrome, Rett syndrome, pervasive developmental disorders, aging-related brain disease, and developmental brain disease, burnout syndrome, carbon monoxide poisoning, cardiac arrest or insufficiency and hemorrhagic shock (global brain ischemia), cataract formation and aging of the eye, central nervous system disease, cerebrovascular disease, chronic fatigue syndrome, chronic stress, cognitive disorders, convulsive disorders, such as variants of grand mal and petit mal epilepsy and Partial Complex Epilepsy, diabetes mellitus, disease of the nervous system (e.g., dyskinesia, L-DOPA induced movement disorders, drug addiction, pain and cataract), drug dependence, drug withdrawal, feeding disorders, Guillain Barr Syndrome and other neuropathies, immune disease, immunitary disorders and therapeutic treatment aimed at modifying biological responses (for instance administrations of interferons or interleukins), inflammatory disorders of the central and/or peripheral nervous system, Injury (trauma, polytrauma), Mental and behavioral disorders, metabolic disease, pain disease, or disorder selected from a group of inflammatory pain, neurophathic pain or migraine, allodynia, hyperalgesia pain, phantom pain, neuropathic pain related to diabetic neuropathy, multiple organ failure, near drowning, necrosis, neoplasms of the brain, neoplastic disorders including lymphomas and other malignant blood disorders, nervous system disease (high-pressure neurological Syndrome, infection), nicotine addiction and other addictive disorders including alcoholism, cannabis, benzodiazepine, barbiturate, morphine and cocaine dependence, change in appetite, sleep disorders, changes in sleep pattern, lack of energy, fatigue, low self-esteem, self-reproach inappropriate guilt, frequent thoughts of death or suicide, plans or attempts to commit suicide, feelings of hopelessness and worthlessness, psychomotor agitation or retardation, diminished capacity for thinking, concentration, or decisiveness, as a neuroprotective agent, spinal cord disease, systemic lupus erythematosis, traumatic damage to the brain and spinal cord, and tremor syndromes, poor balance, brakykinesia, rigidity, tremor, change in speech, loss of facial expression, micrographia, difficulty swallowing, drooling, confusion, fear, sexual dysfunction, language impairment, impairment in decision making, violent outbursts, aggression, hallucination, apathy, impairment in abstract thinking.

Further such conditions or disorders also include, for example, cardiovascular diseases, which refer to diseases and disorders of the heart and circulatory system. These diseases are often associated with dyslipoproteinemias and/or dyslipidemias. Cardiovascular diseases include, but are not limited to, cardiomegaly, atherosclerosis, myocardial infarction, and congestive heart failure, coronary heart disease, hypertension and hypotension.

In particular, such conditions or disorders include conditions or disorders where elevated levels of tryptophan metabolites have been correlated with severity of disease and poor prognosis, including shock, trauma in patients with multiple organ failure, severe acute pancreatitis and chronic kidney disease (Logters, T. T., et al. (2009) *Shock* 32: 29-34, Dabrowski et al (2014) Inflammation 37: 223-234, Changsirivathanathamrong et al (2011) Critical Care Medicine 39: 2678-2683, Mole, D. J., et al. (2008) *Br J Surg* 95: 855-867, Zhao (2013) Renal Failure 35: 648-653, Pawlak, K. et al (2009) Blood Coagulation and Fibrinolysis 20: 590-594, Kabayashi, T. et al (2014) Biochemical and Biophysical Research Communications 445: 412-416).

The methods of treatment of the invention comprise administering a therapeutically effective amount of a compound of formula (I), or a pharmaceutically acceptable salt thereof, to a patient in need thereof. Individual embodiments of the invention include methods of treating any one of the above-mentioned disorders by administering a therapeutically effective amount of a compound of formula (I), or a pharmaceutically acceptable salt thereof, to a patient in need thereof.

As used herein, 'treat' or 'treatment' in reference to a disorder means: (1) to ameliorate or prevent the disorder or one or more of the biological manifestations of the disorder, (2) to interfere with (a): one or more points in the biological cascade that leads to or is responsible for the disorder, or (b):

one or more of the biological manifestations of the disorder, (3) to alleviate one or more of the symptoms or effects associated with the disorder, or (4) to slow the progression of the disorder or one or more of the biological manifestations of the disorder.

As indicated above, 'treatment' of a disorder includes prevention or prophylaxis of the disorder. It will be appreciated that 'prevention' is not an absolute term. In medicine, 'prevention' is understood to refer to the prophylactic administration of a drug to substantially diminish the likelihood or severity of a disorder or biological manifestation thereof, or to delay the onset of such disorder or biological manifestation thereof.

As used herein, 'effective amount' in reference to a compound of formula (I), or a pharmaceutically acceptable salt thereof, or other pharmaceutically-active agent means an amount of the compound sufficient to treat the patient's condition within the scope of sound medical judgment. An effective amount of a compound will vary with the particular compound chosen (for example, the potency, efficacy, and half-life of the compound will be considered); the route of administration chosen; the disorder being treated; the severity of the disorder being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein "patient" refers to a human (including adults and children) or other mammal. In one embodiment, "patient" refers to a human.

The invention further provides, in a further aspect, a method for the treatment of a condition or disorder mediated via KMO (such as the aforementioned disorders), which method comprises administering to a patient in need thereof a therapeutically effective amount of a compound of formula (I) or a pharmaceutically acceptable salt thereof.

In one embodiment there is provided a method for the treatment of acute pancreatitis, chronic kidney disease, acute kidney disease, acute kidney injury, other conditions associated with systemic inflammatory response syndrome (SIRS), Huntington's disease, Alzheimer's disease, spinocerebellar ataxias, Parkinson's disease, AIDS-dementia complex, HIV infection, amylotrophic lateral sclerosis (ALS), depression, schizophrenia, sepsis, cardiovascular shock, severe trauma, acute lung injury, acute respiratory distress syndrome, acute cholecystitis, severe burns, pneumonia, extensive surgical procedures, ischemic bowel disease, severe acute hepatic disease, severe acute hepatic encephalopathy or acute renal failure, which method comprises administering to a patient in need thereof an effective amount of a compound of formula (I) or a pharmaceutically acceptable salt thereof.

In one embodiment there is provided a method for the treatment of acute pancreatitis, which method comprises administering to a patient in need thereof a therapeutically effective amount of a compound of formula (I) or a pharmaceutically acceptable salt thereof.

In one embodiment there is provided a method for the treatment of chronic kidney disease, which method comprises administering to a patient in need thereof a therapeutically effective amount of a compound of formula (I) or a pharmaceutically acceptable salt thereof.

In one embodiment there is provided a method for the treatment of acute pancreatitis, which method comprises administering to a patient in need thereof a therapeutically effective amount of (R)-3-(6-chloro-7-(1-(5-chloropyridin-2-yl)propoxy)-3-oxo-2H-benzo[b][1,4]oxazin-4(3H)-yl)propanoic acid or a pharmaceutically acceptable salt thereof.

In one embodiment there is provided a method for the treatment of chronic kidney disease, which method comprises administering to a patient in need thereof a therapeutically effective amount of (R)-3-(6-chloro-7-(1-(5-chloropyridin-2-yl)propoxy)-3-oxo-2H-benzo[b][1,4]oxazin-4(3H)-yl)propanoic acid or a pharmaceutically acceptable salt thereof.

In a further aspect, there is provided a compound of formula (I) or a pharmaceutically acceptable salt thereof for use in therapy.

In one embodiment, there is provided a compound of formula (I) or a pharmaceutically acceptable salt thereof for use in the treatment of a condition or disorder mediated via KMO.

In one embodiment there is provided a compound of formula (I) or a pharmaceutically acceptable salt thereof for use in the treatment of acute pancreatitis, chronic kidney disease, acute kidney disease, acute kidney injury, other conditions associated with systemic inflammatory response syndrome (SIRS), Huntington's disease, Alzheimer's disease, spinocerebellar ataxias, Parkinson's disease, AIDS-dementia complex, HIV infection, amylotrophic lateral sclerosis (ALS), depression, schizophrenia, sepsis, cardiovascular shock, severe trauma, acute lung injury, acute respiratory distress syndrome, acute cholecystitis, severe burns, pneumonia, extensive surgical procedures, ischemic bowel disease, severe acute hepatic disease, severe acute hepatic encephalopathy or acute renal failure.

In one embodiment there is provided a compound of formula (I) or a pharmaceutically acceptable salt thereof for use in the treatment of acute pancreatitis.

In one embodiment there is provided a compound of formula (I) or a pharmaceutically acceptable salt thereof for use in the treatment of chronic kidney disease.

In one embodiment there is provided (R)-3-(6-chloro-7-(1-(5-chloropyridin-2-yl)propoxy)-3-oxo-2H-benzo[b][1,4]oxazin-4(3H)-yl)propanoic acid or a pharmaceutically acceptable salt thereof for use in the treatment of acute pancreatitis.

In one embodiment there is provided (R)-3-(6-chloro-7-(1-(5-chloropyridin-2-yl)propoxy)-3-oxo-2H-benzo[b][1,4]oxazin-4(3H)-yl)propanoic acid or a pharmaceutically acceptable salt thereof for use in the treatment of chronic kidney disease.

In a further aspect, there is provided the use of a compound of formula (I) or a pharmaceutically acceptable salt thereof in the manufacture of a medicament for the treatment of a condition or disorder mediated via KMO.

In one embodiment there is provided the use of a compound of formula (I) or a pharmaceutically acceptable salt thereof in the manufacture of a medicament for use in the treatment of acute pancreatitis, chronic kidney disease, acute kidney disease, acute kidney injury, other conditions associated with systemic inflammatory response syndrome (SIRS), Huntington's disease, Alzheimer's disease, spinocerebellar ataxias, Parkinson's disease, AIDS-dementia complex, HIV infection, amylotrophic lateral sclerosis (ALS), depression, schizophrenia, sepsis, cardiovascular shock, severe trauma, acute lung injury, acute respiratory distress syndrome, acute cholecystitis, severe burns, pneumonia, extensive surgical procedures, ischemic bowel disease, severe acute hepatic disease, severe acute hepatic encephalopathy or acute renal failure.

In one embodiment there is provided the use of a compound of formula (I) or a pharmaceutically acceptable salt thereof in the manufacture of a medicament for use in the treatment of acute pancreatitis.

In one embodiment there is provided the use of a compound of formula (I) or a pharmaceutically acceptable salt thereof in the manufacture of a medicament for use in the treatment of chronic kidney disease.

In one embodiment there is provided the use of (R)-3-(6-chloro-7-(1-(5-chloropyridin-2-yl)propoxy)-3-oxo-2H-benzo[b][1,4]oxazin-4(3H)-yl)propanoic acid or a pharmaceutically acceptable salt thereof in the manufacture of a medicament for use in the treatment of acute pancreatitis.

In one embodiment there is provided the use of (R)-3-(6-chloro-7-(1-(5-chloropyridin-2-yl)propoxy)-3-oxo-2H-benzo[b][1,4]oxazin-4(3H)-yl)propanoic acid or a pharmaceutically acceptable salt thereof in the manufacture of a medicament for use in the treatment of chronic kidney disease.

A particular compound of the invention for use in the aforementioned methods of treatment is (R)-3-(6-chloro-7-(1-(5-chloropyridin-2-yl)propoxy)-3-oxo-2H-benzo[b][1,4]oxazin-4(3H)-yl)propanoic acid or a pharmaceutically acceptable salt thereof.

Methods and/or Uses Additional Aspects and/or Embodiments

In general, the present invention relates to methods for treating pancreatitis, kidney diseases and other various disorders as described herein, for conditions or disorders mediated by KMO inhibitors, which comprises administering 6-chlorobenzoxazine compounds of Formula (I) or pharmaceutically acceptable salts or pharmaceutical compositions thereof.

In another aspect, the present invention relates to a method or use for treating acute pancreatitis, chronic kidney disease, acute kidney disease, acute kidney injury, other conditions associated with systemic inflammatory response syndrome (SIRS), Huntington's disease, Alzheimer's disease, spinocerebellar ataxias, Parkinson's disease, AIDS-dementia complex, HIV infection, amylotrophic lateral sclerosis (ALS), depression, schizophrenia, sepsis, cardiovascular shock, severe trauma, acute lung injury, severe respiratory distress syndrome, acute cholecystitis, severe burns, pneumonia, extensive surgical procedures, ischemic bowel disease, severe acute hepatic disease, severe acute hepatic encephalopathy or acute renal failure, which comprises administering a therapeutically effective amount of a compound of Formula (I):

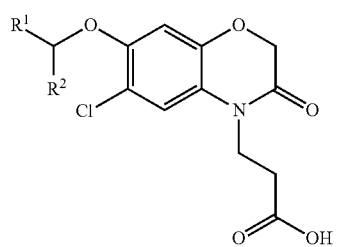

where:
R$^1$ is heteroaryl optionally substituted by methyl, ethyl, or halo; and
R$^2$ is H, methyl or ethyl; or
a pharmaceutically acceptable salt thereof to a patient in need thereof.

In one aspect, the present invention further relates to a method or use for treating pancreatitis, which comprises administering a compound of Formula (I):

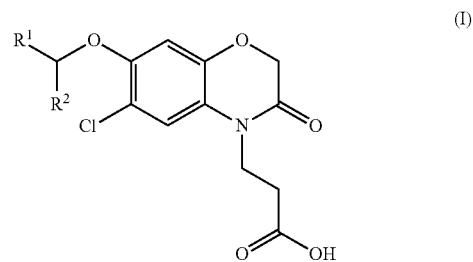

where:
R$^1$ is heteroaryl optionally substituted by methyl, ethyl, or halo; and
R$^2$ is H, methyl or ethyl; or
a pharmaceutically acceptable salt thereof to a patient in need thereof.

In another aspect, the present invention relates to a method or use for treating pancreatitis, kidney disease or other various diseases as defined herein, where:
the heteroaryl as defined for R1 is selected from the group consisting of oxazolyl, pyridinyl, pyrimidinyl, pyridazinyl and imidazolyl;
where:
the oxazolyl, pyridinyl, pyrimidinyl, and pyridazinyl, respectively, is optionally substituted by methyl, ethyl, chloro or fluoro.

In another aspect, the present invention relates to a method or use for treating pancreatitis, kidney disease or other various diseases as defined herein, where R$^1$ is pyridinyl optionally substituted by ethyl, methyl, chloro or fluoro.

In another aspect, the present invention relates to a method or use for treating pancreatitis, kidney disease or other various diseases as defined herein, where R$^2$ is ethyl.

In another aspect, the present invention relates to a method or use for treating pancreatitis, where a compound of Formula (I) is selected from:

(3-(6-chloro-7-(1-(5-chloropyridin-2-yl)propoxy)-3-oxo-2H-benzo[b][1,4]oxazin-4(3H)-yl)propanoic acid;

3-{6-chloro-3-oxo-7-[1-(pyridin-2-yl)ethoxy]-3,4-dihydro-2H-1,4-benzoxazin-4-yl}propanoic acid;

3-{6-chloro-7-[1-(2-methyl-1,3-oxazol-5-yl)ethoxy]-3-oxo-3,4-dihydro-2H-1,4-benzoxazin-4-yl}propanoic acid;

3-{6-chloro-7-[1-(1,3-oxazol-2-yl)ethoxy]-3-oxo-3,4-dihydro-2H-1,4-benzoxazin-4-yl}propanoic acid;

3-{6-chloro-7-[1-(1H-imidazol-2-yl)ethoxy]-3-oxo-3,4-dihydro-2H-1,4-benzoxazin-4-yl}propanoic acid;

3-{6-chloro-3-oxo-7-[1-(pyrimidin-2-yl)ethoxy]-3,4-dihydro-2H-1,4-benzoxazin-4-yl}propanoic acid;

3-[6-chloro-3-oxo-7-(pyridin-2-ylmethoxy)-3,4-dihydro-2H-1,4-benzoxazin-4-yl]propanoic acid;

3-{6-chloro-7-[1-(5-methylpyridin-2-yl)ethoxy]-3-oxo-3,4-dihydro-2H-1,4-benzoxazin-4-yl}propanoic acid;

3-{6-chloro-7-[1-(5-chloropyridin-2-yl)ethoxy]-3-oxo-3,4-dihydro-2H-1,4-benzoxazin-4-yl}propanoic acid;

3-{6-chloro-7-[1-(5-fluoropyridin-2-yl)ethoxy]-3-oxo-3,4-dihydro-2H-1,4-benzoxazin-4-yl}propanoic acid;

3-{6-chloro-3-oxo-7-[1-(pyridazin-3-yl)ethoxy]-3,4-dihydro-2H-1,4-benzoxazin-4-yl}propanoic acid;

3-{6-chloro-7-[(6-methylpyridazin-3-yl)methoxy]-3-oxo-3,4-dihydro-2H-1,4-benzoxazin-4-yl}propanoic acid;

3-{6-chloro-7-[1-(6-methylpyridazin-3-yl)ethoxy]-3-oxo-3,4-dihydro-2H-1,4-benzoxazin-4-yl}propanoic acid;

3-{6-chloro-7-[1-(5-methylpyridin-2-yl)propoxy]-3-oxo-3,4-dihydro-2H-1,4-benzoxazin-4-yl}propanoic acid;

3-{6-chloro-3-oxo-7-[1-(pyridin-2-yl)propoxy]-3,4-dihydro-2H-1,4-benzoxazin-4-yl}propanoic acid;

3-{6-chloro-7-[(5-chloropyridin-2-yl)methoxy]-3-oxo-3,4-dihydro-2H-1,4-benzoxazin-4-yl}propanoic acid;

3-{6-chloro-7-[(5-methylpyridin-2-ylmethoxy]-3-oxo-3,4-dihydro-2H-1,4-benzoxazin-4-yl}propanoic acid;

3-{6-chloro-7-[1-(5-ethylpyridin-2-yl)ethoxy]-3-oxo-3,4-dihydro-2H-1,4-benzoxazin-4-yl}propanoic acid;

3-{6-chloro-3-oxo-7-[1-(pyrimidin-2-yl)propoxy]-3,4-dihydro-2H-1,4-benzoxazin-4-yl}propanoic acid;

3-{6-chloro-7-[1-(5-methylpyrimidin-2-yl)propoxy]-3-oxo-3,4-dihydro-2H-1,4-benzoxazin-4-yl}propanoic acid;

3-{6-chloro-7-[1-(5-chloropyrimidin-2-yl)propoxy]-3-oxo-3,4-dihydro-2H-1,4-benzoxazin-4-yl}propanoic acid;

3-{6-chloro-3-oxo-7-[1-(pyridazin-3-yl)propoxy]-3,4-dihydro-2H-1,4-benzoxazin-4-yl}propanoic acid;

3-{6-chloro-7-[1-(6-methylpyridazin-3-yl)propoxy]-3-oxo-3,4-dihydro-2H-1,4-benzoxazin-4-yl}propanoic acid; or a pharmaceutically acceptable salt thereof to a patient in need thereof.

In another aspect, the present invention relates to a method or use for treating pancreatitis, where the compound is (R)-3-(6-chloro-7-(1-(5-chloropyridin-2-yl)propoxy)-3-oxo-2H-benzo[b][1,4]oxazin-4(3H)-yl)propanoic acid as shown below:

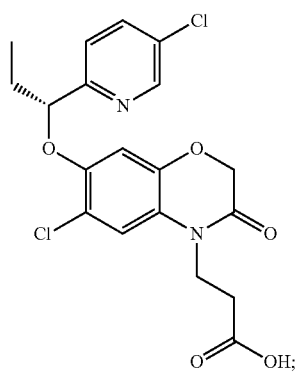 [SMILES: CC[C@@H](Oc1cc2c(cc1Cl)N(CCC(=O)O)C(=O)CO2)c1ccc(Cl)cn1]

or a pharmaceutically acceptable salt thereof.

In another aspect, the present invention relates to a method or use for treating pancreatitis, where the compound is (R)-3-(6-chloro-7-(1-(5-chloropyridin-2-yl)propoxy)-3-oxo-2H-benzo[b][1,4]oxazin-4(3H)-yl)propanoic acid as shown below:

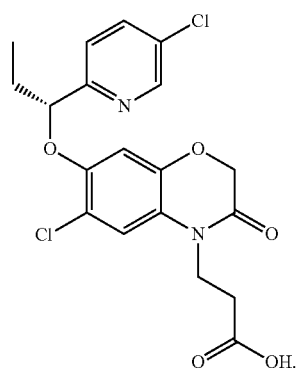 [SMILES: CC[C@@H](Oc1cc2c(cc1Cl)N(CCC(=O)O)C(=O)CO2)c1ccc(Cl)cn1]

In another aspect, the present invention relates to a method or use for treating pancreatitis, where the compound is (R)-3-(6-Chloro-7-(1-(5-chloropyridin-2-yl)propoxy)-3-oxo-2H-benzo[b][1,4]oxazin-4(3H)-yl)propanoic acid as shown below:

or a pharmaceutically acceptable salt thereof.

In another aspect, the present invention relates to a method or use for treating pancreatitis, wherein the pancreatitis is acute pancreatitis.

In another aspect, the present invention relates to a method or use for treating acute pancreatitis.

In another aspect, the present invention relates to a method or use for treating pancreatitis, which comprises administering a therapeutically effective amount of a pharmaceutical composition to a patient, where the pharmaceutical composition comprises:

a) a therapeutically effective amount of a compound of Formula (I):

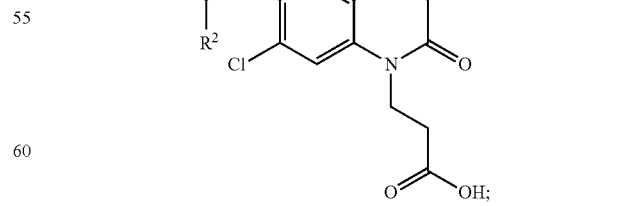

where:
R$^1$ is heteroaryl optionally substituted by methyl, ethyl, or halo;
R$^2$ is H, methyl or ethyl; or a pharmaceutically acceptable salt thereof to a patient in need thereof; and b) a at least one pharmaceutically acceptable excipient(s).

In another aspect, the present invention relates to a method or use for treating pancreatitis, where the pancreatitis is acute pancreatitis.

In another aspect, the present invention relates to a method or use for acute treating pancreatitis.

In another aspect, the present invention relates to a method or use for treating kidney disease, which comprises administering a compound of Formula (I):

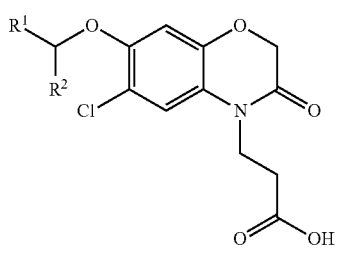

where:
R¹ is heteroaryl optionally substituted by methyl, ethyl, or halo; and
R² is H, methyl or ethyl; or
a pharmaceutically acceptable salt thereof to a patient in need thereof.

In another aspect, the present invention relates to a method or use for treating kidney disease, where:
the heteroaryl as defined for R¹ is selected from the group consisting of oxazolyl, pyridinyl, pyrimidinyl, pyridazinyl and imidazolyl,
where:
the oxazolyl, pyridinyl, pyrimidinyl, and pyridazinyl, respectively, is optionally substituted by methyl, ethyl, chloro or fluoro.

In another aspect, the present invention relates to a method or use for treating kidney disease, where R¹ is pyridinyl optionally substituted by ethyl, methyl, chloro or fluoro.

In another aspect, the present invention relates to a method or use for treating kidney disease, where R² is ethyl.

In another aspect, the present invention relates to a method or use for treating kidney disease, where the kidney disease is selected from chronic kidney disease, acute kidney disease, acute kidney injury.

In another aspect, the present invention relates to a method or for treating kidney disease, where the compound of Formula (I) is selected from:
(3-(6-chloro-7-(1-(5-chloropyridin-2-yl)propoxy)-3-oxo-2H-benzo[b][1,4]oxazin-4(3H)-yl)propanoic acid;
3-{6-chloro-3-oxo-7-[1-(pyridin-2-yl)ethoxy]-3,4-dihydro-2H-1,4-benzoxazin-4-yl}propanoic acid;
3-{6-chloro-7-[1-(2-methyl-1,3-oxazol-5-yl)ethoxy]-3,4-dihydro-2H-1,4-benzoxazin-4-yl}propanoic acid;
3-{6-chloro-7-[1-(1,3-oxazol-2-yl)ethoxy]-3-oxo-3,4-dihydro-2H-1,4-benzoxazin-4-yl}propanoic acid;
3-{6-chloro-7-[1-(1H-imidazol-2-yl)ethoxy]-3-oxo-3,4-dihydro-2H-1,4-benzoxazin-4-yl}propanoic acid;
3-{6-chloro-3-oxo-7-[1-(pyrimidin-2-yl)ethoxy]-3,4-dihydro-2H-1,4-benzoxazin-4-yl}propanoic acid;
3-[6-chloro-3-oxo-7-(pyridin-2-ylmethoxy)-3,4-dihydro-2H-1,4-benzoxazin-4-yl]propanoic acid;
3-{6-chloro-7-[1-(5-methylpyridin-2-yl)ethoxy]-3-oxo-3,4-dihydro-2H-1,4-benzoxazin-4-yl}propanoic acid;
3-{6-chloro-7-[1-(5-chloropyridin-2-yl)ethoxy]-3-oxo-3,4-dihydro-2H-1,4-benzoxazin-4-yl}propanoic acid;
3-{6-chloro-7-[1-(5-fluoropyridin-2-yl)ethoxy]-3-oxo-3,4-dihydro-2H-1,4-benzoxazin-4-yl}propanoic acid;
3-{6-chloro-3-oxo-7-[1-(pyridazin-3-yl)ethoxy]-3,4-dihydro-2H-1,4-benzoxazin-4-yl}propanoic acid;
3-{6-chloro-7-[(6-methylpyridazin-3-yl)methoxy]-3-oxo-3,4-dihydro-2H-1,4-benzoxazin-4-yl}propanoic acid;
3-{6-chloro-7-[1-(6-methylpyridazin-3-yl)ethoxy]-3-oxo-3,4-dihydro-2H-1,4-benzoxazin-4-yl}propanoic acid;
3-{6-chloro-7-[1-(5-methylpyridin-2-yl)propoxy]-3-oxo-3,4-dihydro-2H-1,4-benzoxazin-4-yl}propanoic acid;
3-{6-chloro-3-oxo-7-[1-(pyridin-2-yl)propoxy]-3,4-dihydro-2H-1,4-benzoxazin-4-yl}propanoic acid;
3-{6-chloro-7-[(5-chloropyridin-2-ylmethoxy]-3-oxo-3,4-dihydro-2H-1,4-benzoxazin-4-yl}propanoic acid;
3-{6-chloro-7-[(5-methylpyridin-2-yl)methoxy]-3-oxo-3,4-dihydro-2H-1,4-benzoxazin-4-yl}propanoic acid;
3-{6-chloro-7-[1-(5-ethylpyridin-2-yl)ethoxy]-3-oxo-3,4-dihydro-2H-1,4-benzoxazin-4-yl}propanoic acid;
3-{6-chloro-3-oxo-7-[1-(pyrimidin-2-yl)propoxy]-3,4-dihydro-2H-1,4-benzoxazin-4-yl}propanoic acid;
3-{6-chloro-7-[1-(5-methylpyrimidin-2-yl)propoxy]-3-oxo-3,4-dihydro-2H-1,4-benzoxazin-4-yl}propanoic acid;
3-{6-chloro-7-[1-(5-chloropyrimidin-2-yl)propoxy]-3-oxo-3,4-dihydro-2H-1,4-benzoxazin-4-yl}propanoic acid;
3-{6-chloro-3-oxo-7-[1-(pyridazin-3-yl)propoxy]-3,4-dihydro-2H-1,4-benzoxazin-4-yl}propanoic acid;
3-{6-chloro-7-[1-(6-methylpyridazin-3-yl)propoxy]-3-oxo-3,4-dihydro-2H-1,4-benzoxazin-4-yl}propanoic acid; or
a pharmaceutically acceptable salt thereof to a patient in need thereof.

In another aspect, the present invention relates to a method for treating kidney disease, where the kidney disease is selected from chronic kidney disease, acute kidney disease, acute kidney injury.

In another aspect, the present invention relates to a method or use for treating kidney disease, where the compound is (R)-3-(6-Chloro-7-(1-(5-chloropyridin-2-yl)propoxy)-3-oxo-2H-benzo[b][1,4]oxazin-4(3H)-yl)propanoic acid as shown below:

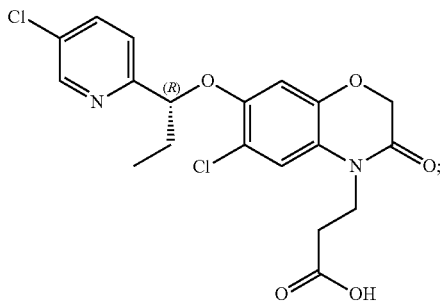

or
a pharmaceutically acceptable salt thereof.

In another aspect, the present invention relates to a method or use for treating kidney disease according to claim 17, where the compound is (R)-3-(6-Chloro-7-(1-(5-chloropyridin-2-yl)propoxy)-3-oxo-2H-benzo[b][1,4]oxazin-4(3H)-yl)propanoic acid as shown below:

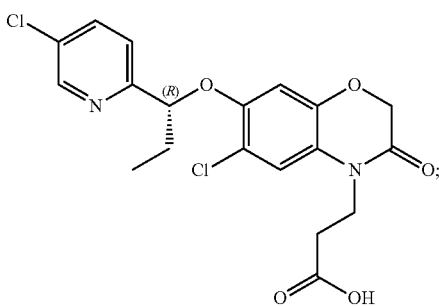

or a pharmaceutically acceptable salt thereof.

In another aspect, the present invention relates to a method or use for treating kidney disease, which comprises administering a therapeutically effective amount of a pharmaceutical composition to a patient, where the pharmaceutical composition comprises:
  a) a therapeutically effective amount of a compound of Formula (I):

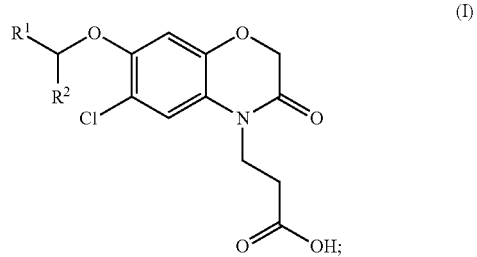

where:
  $R^1$ is heteroaryl optionally substituted by methyl, ethyl, or halo;
  $R^2$ is H, methyl or ethyl; or
  a pharmaceutically acceptable salt thereof to a patient in need thereof; and
  b) a at least one pharmaceutically acceptable excipient(s).

Compositions

The compounds of the invention will normally, but not necessarily, be formulated into pharmaceutical compositions prior to administration to a patient. Accordingly, in another aspect, there is provided a pharmaceutical composition comprising a compound of formula (I) or a pharmaceutically acceptable salt thereof and one or more pharmaceutically acceptable excipients. The pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of formula (I) or pharmaceutically acceptable salts thereof once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: Diluents, fillers, binders, disintegrants, lubricants, glidants, granulating agents, coating agents, wetting agents, solvents, co-solvents, suspending agents, emulsifiers, sweeteners, flavouring agents, flavour-masking agents, colouring agents, anti-caking agents, humectants, chelating agents, plasticisers, viscosity increasing agents, antioxidants, preservatives, stabilisers, surfactants, and buffering agents. The skilled artisan will appreciate that certain pharmaceutically acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in Remington's Pharmaceutical Sciences (Mack Publishing Company).

The pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories.

The pharmaceutical composition of the invention may contain from 0.1% to 99% by weight, of the active material, depending on the method of administration. The dose of the compound used in the treatment of the aforementioned conditions or disorders will vary in the usual way with the seriousness of the conditions or disorders, the weight of the subject, and other similar factors. However, as a general guide suitable unit doses may be 0.05 to 5000 mg, 1.0 to 500 mg or 1.0 to 200 mg and such unit doses may be administered more than once a day, for example two or three times a day. Such therapy may extend for a number of weeks, months or years.

In one embodiment injectable or infusible solutions, or reconstitutable powders, are preferred.

In one embodiment, a composition adapted for oral formulation is preferred.

Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound.

For parenteral administration, fluid unit dosage forms are prepared utilising a compound of the invention or pharmaceutically acceptable salt thereof and a sterile vehicle. Formulations for injection may be presented in unit dosage form e.g. in ampoules or in multi-dose, utilising a compound of the invention or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device. Thus compounds of formula (I) may be formulated for oral, buccal, parenteral, topical (including ophthalmic and nasal), depot or rectal administration or in a form suitable for administration by inhalation or insufflation (either through the mouth or nose).

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

The invention provides for a pharmaceutical composition for use in the treatment of acute pancreatitis, chronic kidney disease, acute kidney disease, acute kidney injury, other conditions associated with systemic inflammatory response syndrome (SIRS), Huntington's disease, Alzheimer's disease, spinocerebellar ataxias, Parkinson's disease, AIDS-dementia complex, HIV infection, amylotrophic lateral sclerosis (ALS), depression, schizophrenia, sepsis, cardiovascular shock, severe trauma, acute lung injury, acute respiratory distress syndrome, acute cholecystitis, severe burns, pneumonia, extensive surgical procedures, ischemic bowel disease, severe acute hepatic disease, severe acute hepatic encephalopathy or acute renal failure which comprises a compound of formula (I) or a pharmaceutically acceptable salt thereof and one or more pharmaceutically acceptable excipients.

Biological Data

KMO inhibition can be determined by MS Rapidfire assay performed on the human cloned enzyme as described herein. Compounds of formula (I) have demonstrated inhibitory activity at the KMO enzyme, using the MS Rapidfire functional assay described herein, or a substantially similar assay.

KMO MS Rapidfire Assay Protocol

Materials and Methods

Materials

L-Kynurenine (Kyn), 3-hydroxy-DL-kynurenine (3-HK), β-Nicotinamide adenine dinucleotide 2'-phosphate reduced tetrasodium salt hydrate (NADPH), 4-(2-hydroxyethyl)piperazine-1-ethanesulfonic acid (HEPES), DL-dithiothreitol (DTT), ethylenediaminetetraacetic acid (EDTA), CHAPS and trifluoroacetic acid (TFA) were purchased from Sigma-Aldrich Ltd. (Gillingham, Dorset, UK). HPLC-grade acetonitrile and formic acid were supplied by Fisher Scientific (Loughborough, UK).

Cloning and Expression of Human KMO

Full length human KMO was amplified by PCR from pcDNA5/FRTN5-His-TOPO/hKMO (vector supplied by the University of Edinburgh) and cloned into pGEX6P-1 (GE Healthcare) using BamH1 and Sal1 restriction sites. DNA encoding the N-terminal Glutathione-S-transferase (GST) tag, followed by a Pre-Scission protease cleavage site, and the full length KMO was amplified by PCR from pGEX6P-1-KMO and cloned into pFastbac1 (Invitrogen) using Xbal and EcoR1 restriction sites.

pFastbac1 GST-KMO was transposed into the baculovirus genome using the BAC-to-BAC technology (Invitrogen) and bacmid DNA was prepared and transfected into Spodoptera frugiperda (Sf9) cells using Cellfectin II (Invitrogen). Expression of a protein of the expected molecular weight (Mr 82,634) was seen by Western blot analysis using anti-GST-peroxidase conjugate.

Preparation of Membranes from Sf9 Cells Expressing Human GST-KMO

A P1 virus stock was generated from a single clone and used to infect 3×1.5 L cultures of Sf9 cells in 3 L Corning Fernbach flasks. The Sf9 cells were grown in Hyclone SFX media (Thermo Scientific) to about 3×10$^6$ cells/ml and were infected at a nominal multiplicity of infection of 3. Cells were harvested after 48 hours and disrupted by blending in 50 mM HEPES, pH 7.4, 1 mM EDTA buffer containing protease inhibitors. A low speed spin (400 g) was used to remove cell debris, followed by a high speed spin (75000 g) to pellet the membranes. The membranes were purified in a discontinuous sucrose density gradient by re-suspending in 10% (w/v) sucrose and layering over 40% (w/v) sucrose, both in the above buffer. This was centrifuged at 150000 g and the purified membranes were taken from the interface, collected by centrifugation at 100000 g, resuspended in buffer and aliquoted for storage at −80° C. KMO activity was found to be associated with the membrane fraction only and no KMO activity was detected in membranes prepared from uninfected Sf9 cells. A batch of 104 mg of purified Sf9 KMO-membranes (as determined by the Pierce BCA protein assay using bovine serum albumin as standard) was prepared and validated in the RapidFire High-Throughput Mass Spectrometry (RF MS) assay.

RapidFire High-Throughput Mass Spectrometry Assay

Method 1

11 point, 3-fold serial dilutions of test compounds were prepared in DMSO and 100 nL of these solutions were dispensed into 384-well V-base polypropylene plates (Greiner Bio-one, Stonehouse, UK) using an Echo 555 acoustic dispenser (Labcyte, Sunnyvale, Calif.). This gave a final assay concentration range between 100 μM and 1.7 nM in 10 μL final assay volume (see below). 100 nL DMSO was dispensed into columns 6 and 18 for high and low controls, respectively, with prior inactivation of the enzyme in column 18 by pre-dispense of 30 μL of 0.5% (v/v) TFA.

Conditions for the assay of human KMO using isolated KMO-membranes were 50 mM HEPES, pH 7.5, 2 mM DTT, 1 mM EDTA, 100 μM CHAPS, 200 μM NADPH, 10 μM Kynurenine and 8 μg/ml KMO-membranes in a total reaction volume of 10 μL.

Assays were performed by initially dispensing 5 μL of a 2× Enzyme solution (16 μg/ml KMO-membranes in 50 mM HEPES, pH 7.5, 2 mM DTT, 2 mM EDTA, 200 μM CHAPS) into plates containing 100 nL compounds and incubating for 10 min at ambient temperature. Reactions were initiated by addition of 5 μL of 2× Substrate solution (400 μM NADPH, 20 μM Kynurenine in 50 mM HEPES, pH 7.5, 2 mM DTT) and incubated for 2 h at room temperature before quenching the reaction with 30 μL of 0.5% (v/v) TFA. Plates were centrifuged at 2500 rpm for 10 min before analysis. All additions were made using a Multidrop Combi dispenser (Thermo Fisher Scientific).

Quenched assay plates were transferred to a high-throughput RapidFire200 integrated autosampler/solid-phase extraction (SPE) system (Agilent Technologies, Wakefield, Mass.). Samples were aspirated from each well for 500 ms and 10 μL was loaded directly onto a RapidFire micro-scale SPE C18 (type C) cartridge, which was washed for 3 s with HPLC-grade water containing 0.1% (v/v) formic acid to remove non-organic components. Analytes were then eluted into the mass spectrometer, in a 3 s elution cycle, using 80% (v/v) acetonitrile/water containing 0.1% (v/v) formic acid, and the cartridge was then equilibrated by washing with water containing 0.1% (v/v) formic acid for 500 ms. This gave a total cycle time of 7 s, enabling analysis of a 384-well plate in approximately 45 min.

Both Kyn and 3-HK were detected using a Sciex AP14000 triple quadrupole mass spectrometer (Applied Biosystems, Concord, Ontario, Canada), equipped with an electrospray interface and operated in positive ion mode. Multiple reaction monitoring (MRM) was used to detect both Kyn and 3-HK using Q1/Q3 transitions at m/z 209.4 to 192.0 and m/z 225.3 to 208.2, respectively. The mass spectrometer used an ESI voltage of 5500 V and a source temperature of 600° C., with a dwell time of 50 ms for each transition.

Data Analysis

Individual MRM transitions were saved as text files and the extracted ion chromatograms were integrated and processed using the RapidFire® peak integration software (version 3.6).

Using the integrated peak area for 3-HK data was analysed within ActivityBase (ID Business Solutions Ltd, Surrey, UK). Dose response curves were fitted to equation (1):

$$\text{Inhibition}(\%) = \frac{(a-d)}{1 + \left(\frac{[I]}{IC_{50}}\right)^S} + d \qquad (1)$$

Where a is the uninhibited response, d is the fully inhibited response, [I] is the inhibitor concentration, $IC_{50}$ is [I] that gives 0.5×(a−d) and S is the Hill slope.

Method 2

11 point, 3-fold serial dilutions of test compounds were prepared in DMSO and 100 nL of these solutions were dispensed into 384-well V-base polypropylene plates (Greiner Bio-one, Stonehouse, UK) using an Echo 555 acoustic dispenser (Labcyte, Sunnyvale, Calif.). This gave a final assay concentration range between 10 μM and 0.17 nM in 10 μL final assay volume (see below). 100 nL DMSO was dispensed into columns 6 and 18 for high and low controls, respectively, with prior inactivation of the enzyme in column 18 by pre-dispense of 50 μL of 0.5% (v/v) TFA.

Conditions for the assay of human KMO using isolated KMO-membranes were 50 mM Hepes, pH 7.5, 2 mM DTT, 1 mM EDTA, 100 μM CHAPS, 200 μM NADPH, 10 μM Kynurenine and 4 μg/ml KMO-membranes in a total reaction volume of 10 μL.

Assays were performed by initially dispensing 5 μL of a 2× Enzyme solution (8 μg/ml KMO-membranes in 50 mM Hepes, pH 7.5, 2 mM DTT, 2 mM EDTA, 200 μM CHAPS) into plates containing 100 nL compounds and incubating for 30 min at ambient temperature. Reactions were initiated by addition of 5 μL of 2× Substrate solution (400 μM NADPH, 20 μM Kynurenine in 50 mM Hepes, pH 7.5, 2 mM DTT) and incubated for 2 h at room temperature before quenching the reaction with 50 μL of 0.5% (v/v) TFA. Plates were centrifuged at 3000 rpm for 10 min before analysis. All additions were made using a Multidrop Combi dispenser (Thermo Fisher Scientific).

Quenched assay plates were transferred to a high-throughput RapidFire200 integrated autosampler/solid-phase extraction (SPE) system (Agilent Technologies, Wakefield, Mass.). Samples were aspirated from each well for 650 ms and approximately 10 μL was loaded directly onto a Rapid-Fire micro-scale SPE C18 (type C) cartridge, which was washed for 1500 ms with HPLC-grade water containing 0.1% (v/v) formic acid to remove non-organic components. Analytes were then eluted into the mass spectrometer, in a 1500 ms elution cycle, using 80% (v/v) acetonitrile/water containing 0.1% (v/v) formic acid, and the cartridge was then equilibrated by washing with water containing 0.1% (v/v) formic acid for 500 ms. This gave a total cycle time of 7 s, enabling analysis of a 384-well plate in approximately 45 min.

Both Kyn and 3-HK were detected using a Sciex AP14000 triple quadrupole mass spectrometer (Sciex, Warrington, Cheshire, UK), equipped with an electrospray interface and operated in positive ion mode. Multiple reaction monitoring (MRM) was used to detect both Kyn and 3-HK using Q1/Q3 transitions at m/z 209.2 to 192.0 and m/z 225.2 to 208.1, respectively. The mass spectrometer used an ESI voltage of 5500 V and a source temperature of 650° C., with a dwell time of 50 ms for each transition.

Data Analysis

Individual MRM transitions were saved as text files and the extracted ion chromatograms were integrated and processed using the RapidFire® peak integration software (version 4.0).

Using the integrated peak area for 3-HK data was analysed within ActivityBase (ID Business Solutions Ltd, Surrey, UK). Dose response curves were fitted to equation (1):

$$\text{Inhibition}(\%) = \frac{(a-d)}{1+\left(\frac{[I]}{IC_{50}}\right)^S} + d \qquad (1)$$

Where a is the uninhibited response, d is the fully inhibited response, [I] is the inhibitor concentration, $IC_{50}$ is [I] that gives 0.5×(a–d) and S is the Hill slope.

The compounds of Examples 1-30 were tested essentially as described in at least one of the above assays. Those of skill in the art will recognise that in vitro binding assays and cell-based assays for functional activity are subject to experimental variability. Accordingly, it is to be understood that the $pIC_{50}$ values given below are exemplary only.

Exemplified compounds of the invention have median $pIC_{50}$ values of ≥5.5 in at least one of the above MS Rapidfire assays.

Examples 1, 2, 2a-2l, 3, 4, 6, 7, 9, 10-20, 21, 23, 26, 28 and 29 had median $pIC_{50}$ values of ≥7.5 in at least one of the above MS Rapidfire assays.

Example 1 had a median $pIC_{50}$ value of 9.0 in at least one of the above MS Rapidfire assays.

What is claimed is:

1. A method for treating pancreatitis, which comprises administering a compound of Formula (I):

wherein:
R¹ is a heteroaryl ring selected from pyrrolyl, triazolyl, thiadiazolyl, tetrazolyl, imidazolyl, pyrazolyl, isothiazolyl, thiazolyl, isoxazolyl, oxazolyl, oxadiazolyl, furazanyl, furanyl, thienyl, pyridyl, pyrimidinyl, pyrazinyl, pyridazinyl or triazinyl;
wherein:
the heteroaryl of R¹ optionally is substituted by methyl, ethyl, or halogen;
R² is H, methyl or ethyl; or
a pharmaceutically acceptable salt thereof to a patient in need thereof.

2. The method for treating pancreatitis according to claim 1, wherein:
the heteroaryl as defined for R1 is selected from the group consisting of oxazolyl, pyridinyl, pyrimidinyl, pyridazinyl and imidazolyl;
wherein:
the oxazolyl, pyridinyl, pyrimidinyl, and pyridazinyl, respectively, is optionally substituted by methyl, ethyl or halogen;
wherein:
halogen is chloro or fluoro.

3. The method for treating pancreatitis according to claim 2, wherein R¹ is pyridinyl optionally substituted by ethyl, methyl, chloro or fluoro.

4. The method for treating pancreatitis according to claim 3, wherein R² is ethyl.

5. The method for treating pancreatitis according to claim 1, wherein the compound of Formula (I) is selected from:
(3-(6-chloro-7-(1-(5-chloropyridin-2-yl)propoxy)-3-oxo-2H-benzo[b][1,4]oxazin-4(3H)-yl)propanoic acid;
3-{6-chloro-3-oxo-7-[1-(pyridin-2-yl)ethoxy]-3,4-dihydro-2H-1,4-benzoxazin-4-yl}propanoic acid;
3-{6-chloro-7-[1-(2-methyl-1,3-oxazol-5-yl)ethoxy]-3-oxo-3,4-dihydro-2H-1,4-benzoxazin-4-yl}propanoic acid;
3-{6-chloro-7-[1-(1,3-oxazol-2-yl)ethoxy]-3-oxo-3,4-dihydro-2H-1,4-benzoxazin-4-yl}propanoic acid;
3-{6-chloro-7-[1-(1H-imidazol-2-yl)ethoxy]-3-oxo-3,4-dihydro-2H-1,4-benzoxazin-4-yl}propanoic acid;
3-{6-chloro-3-oxo-7-[1-(pyrimidin-2-yl)ethoxy]-3,4-dihydro-2H-1,4-benzoxazin-4-yl}propanoic acid;
3-[6-chloro-3-oxo-7-(pyridin-2-ylmethoxy)-3,4-dihydro-2H-1,4-benzoxazin-4-yl]propanoic acid;
3-{6-chloro-7-[1-(5-methylpyridin-2-yl)ethoxy]-3-oxo-3,4-dihydro-2H-1,4-benzoxazin-4-yl}propanoic acid;
3-{6-chloro-7-[1-(5-chloropyridin-2-yl)ethoxy]-3-oxo-3,4-dihydro-2H-1,4-benzoxazin-4-yl}propanoic acid;
3-{6-chloro-7-[1-(5-fluoropyridin-2-yl)ethoxy]-3-oxo-3,4-dihydro-2H-1,4-benzoxazin-4-yl}propanoic acid;
3-{6-chloro-3-oxo-7-[1-(pyridazin-3-yl)ethoxy]-3,4-dihydro-2H-1,4-benzoxazin-4-yl}propanoic acid;
3-{6-chloro-7-[(6-methylpyridazin-3-yl)methoxy]-3-oxo-3,4-dihydro-2H-1,4-benzoxazin-4-yl}propanoic acid;
3-{6-chloro-7-[1-(6-methylpyridazin-3-yl)ethoxy]-3-oxo-3,4-dihydro-2H-1,4-benzoxazin-4-yl}propanoic acid;
3-{6-chloro-7-[1-(5-methylpyridin-2-yl)propoxy]-3-oxo-3,4-dihydro-2H-1,4-benzoxazin-4-yl}propanoic acid;
3-{6-chloro-3-oxo-7-[1-(pyridin-2-yl)propoxy]-3,4-dihydro-2H-1,4-benzoxazin-4-yl}propanoic acid;
3-{6-chloro-7-[(5-chloropyridin-2-yl)methoxy]-3-oxo-3,4-dihydro-2H-1,4-benzoxazin-4-yl}propanoic acid;
3-{6-chloro-7-[(5-methylpyridin-2-yl)methoxy]-3-oxo-3,4-dihydro-2H-1,4-benzoxazin-4-yl}propanoic acid;

3-{6-chloro-7-[1-(5-ethylpyridin-2-yl)ethoxy]-3-oxo-3,4-dihydro-2H-1,4-benzoxazin-4-yl}propanoic acid;
3-{6-chloro-3-oxo-7-[1-(pyrimidin-2-yl)propoxy]-3,4-dihydro-2H-1,4-benzoxazin-4-yl}propanoic acid;
3-{6-chloro-7-[1-(5-methylpyrimidin-2-yl)propoxy]-3-oxo-3,4-dihydro-2H-1,4-benzoxazin-4-yl}propanoic acid;
3-{6-chloro-7-[1-(5-chloropyrimidin-2-yl)propoxy]-3-oxo-3,4-dihydro-2H-1,4-benzoxazin-4-yl}propanoic acid;
3-{6-chloro-3-oxo-7-[1-(pyridazin-3-yl)propoxy]-3,4-dihydro-2H-1,4-benzoxazin-4-yl}propanoic acid;
3-{6-chloro-7-[1-(6-methylpyridazin-3-yl)propoxy]-3-oxo-3,4-dihydro-2H-1,4-benzoxazin-4-yl}propanoic acid; or
a pharmaceutically acceptable salt thereof to a patient in need thereof.

6. The method for treating pancreatitis according to claim 5, wherein the compound is (R)-3-(6-chloro-7-(1-(5-chloropyridin-2-yl)propoxy)-3-oxo-2H-benzo[b][1,4]oxazin-4(3H)-yl)propanoic acid as shown below:

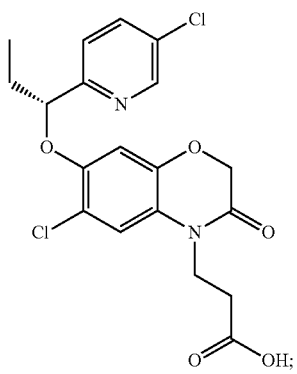

or
a pharmaceutically acceptable salt thereof.

7. The method for treating pancreatitis according to claim 6, wherein the compound is (R)-3-(6-chloro-7-(1-(5-chloropyridin-2-yl)propoxy)-3-oxo-2H-benzo[b][1,4]oxazin-4(3H)-yl)propanoic acid as shown below:

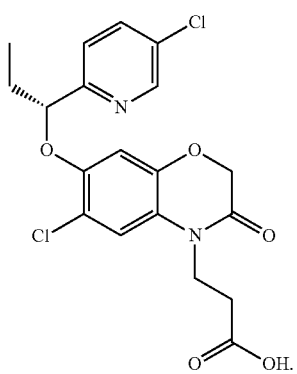 [SMILES: CC[C@@H](Oc1cc2c(cc1Cl)N(CCC(=O)O)C(=O)CO2)c1ccc(Cl)cn1]

8. The method for treating pancreatitis according to claim 5, wherein the compound is (R)-3-(6-Chloro-7-(1-(5-chloropyridin-2-yl)propoxy)-3-oxo-2H-benzo[b][1,4]oxazin-4(3H)-yl)propanoic acid as shown below:

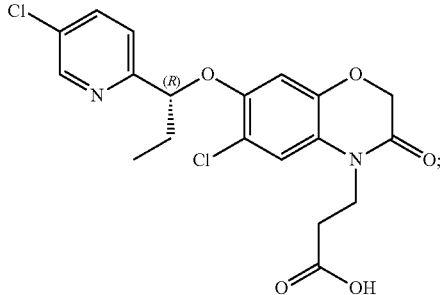

or
a pharmaceutically acceptable salt thereof.

9. The method for treating pancreatitis according to claim 1, wherein the pancreatitis is acute pancreatitis.

10. A method for treating pancreatitis, which comprises administering a therapeutically effective amount of a pharmaceutical composition to a patient, wherein the pharmaceutical composition comprises:

a) a therapeutically effective amount of a compound of Formula (I):

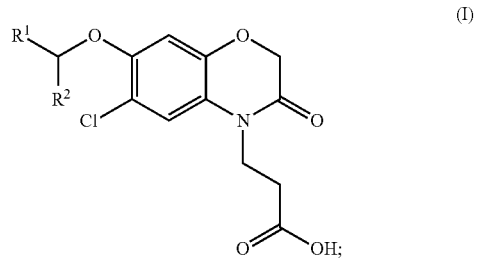

wherein:
R$^1$ is heteroaryl optionally substituted by methyl, ethyl, or halo;
R$^2$ is H, methyl or ethyl; or
a pharmaceutically acceptable salt thereof to a patient in need thereof; and b) at least one pharmaceutically acceptable excipient(s).

11. The method for treating pancreatitis according to claim 10, wherein the pancreatitis is acute pancreatitis.

* * * * *